(12) United States Patent
Ghazaleh et al.

(10) Patent No.: US 11,862,345 B2
(45) Date of Patent: Jan. 2, 2024

(54) MEDICAL TREATMENT METRIC MODELLING BASED ON MACHINE LEARNING

(71) Applicant: Roche Molecular Systems, Inc., Pleasanton, CA (US)

(72) Inventors: Naghmeh Ghazaleh, Basel (CH); Jaya Madala, Cupertino, CA (US); Tyler O'Neill, San Francisco, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 837 days.

(21) Appl. No.: 16/680,962

(22) Filed: Nov. 12, 2019

(65) Prior Publication Data

US 2020/0152320 A1    May 14, 2020

Related U.S. Application Data

(60) Provisional application No. 62/766,985, filed on Nov. 12, 2018.

(51) Int. Cl.
*G16H 50/70* (2018.01)
*G16H 10/60* (2018.01)
(Continued)

(52) U.S. Cl.
CPC ............ *G16H 50/70* (2018.01); *G06F 17/18* (2013.01); *G06F 18/2113* (2023.01);
(Continued)

(58) Field of Classification Search
None
See application file for complete search history.

(56) References Cited

U.S. PATENT DOCUMENTS

| | | | |
|---|---|---|---|
| 11,270,800 B1 * | 3/2022 | Mitidis | ................. A61B 5/0205 |
| 2008/0147441 A1 * | 6/2008 | Kil | ......................... G06Q 40/08 |
| | | | 705/2 |

(Continued)

FOREIGN PATENT DOCUMENTS

| | | | | |
|---|---|---|---|---|
| CN | 108680358 A | * | 10/2018 | |
| CN | 111316281 A | * | 6/2020 | ........... G06F 40/289 |

(Continued)

OTHER PUBLICATIONS

International Search Report and Written Opinion in PCT/US2019/060891 dated Feb. 13, 2020; 14 pages.

(Continued)

*Primary Examiner* — Mohammed Rachedine
(74) *Attorney, Agent, or Firm* — Kilpatrick Townsend and Stockton LLP

(57) ABSTRACT

In one example, an apparatus comprises a treatment metric model database that stores a plurality of treatment metric models, each of the plurality of treatment metric models being generated for a first cluster of cluster features vectors, each cluster feature vector representing a distribution for each of a plurality of data categories of patients data represented by patient feature vectors clustered in a second cluster. The apparatus is further configured to: receive patient characteristics features data of a patient; identify a first treatment metric model based on the patient characteristics features data of the patient; input the first patient characteristic features data and data representing a range of administrations of the treatment to the first treatment metric model to compute a range of the treatment metric; and select an administration of the treatment from the range of administrations of the treatment having optimal treatment metric.

19 Claims, 13 Drawing Sheets

(51) Int. Cl.
*G16H 40/20* (2018.01)
*G06F 17/18* (2006.01)
*G06F 18/2113* (2023.01)
*G06F 18/23213* (2023.01)
*G06F 18/2411* (2023.01)
*G06N 20/10* (2019.01)

(52) U.S. Cl.
CPC .... *G06F 18/23213* (2023.01); *G06F 18/2411* (2023.01); *G06N 20/10* (2019.01); *G16H 10/60* (2018.01); *G16H 40/20* (2018.01)

(56) References Cited

U.S. PATENT DOCUMENTS

| | | |
|---|---|---|
| 2014/0052465 A1 | 2/2014 | Madan et al. |
| 2016/0063212 A1* | 3/2016 | Monier ............... G16H 10/60 705/3 |
| 2017/0270430 A1* | 9/2017 | Llagostera ............ G06N 20/00 |
| 2018/0350075 A1* | 12/2018 | Grimmer ................ G06T 7/40 |

FOREIGN PATENT DOCUMENTS

| | | | | |
|---|---|---|---|---|
| WO | WO-2008091814 A2 * | 7/2008 | ........... | C12Q 1/6883 |
| WO | WO-2019018430 A1 * | 1/2019 | ............ | G06N 20/00 |
| WO | WO-2019142293 A1 * | 7/2019 | ............ | C09B 19/00 |

OTHER PUBLICATIONS

Zheng, P. et al.; "Hound: Causal Learning for Datacenter-scale Straggler Diagnosis"; *Proceedings of the ACM on Measurement and Analysis of Computing Systems*; vol. 2, No. 1; Apr. 3, 2018; pp. 1-36.

* cited by examiner

Demographic data 204

| # | Field | | | | | Vector | # |
|---|---|---|---|---|---|---|---|
| 300 | Age Group | 18-44 | 45-64 | 65-74 | >74 | 1,0,0,0 | 330 |
| 302 | Marital status | Single | Married | Other | | 0,1,0 | 332 |
| 304 | Race | X number of alternatives | | | | 0,...1,...0,0,0,0 | 334 |
| 306 | Gender | Male | Female | Other | | 1,0,0 | 336 |
| 308 | Locale | Y number of alternatives | | | | 0,...1,...0,0,0,0 | 338 |

Diagnostic data 206

| # | Field | | | Vector | # |
|---|---|---|---|---|---|
| 310 | Organ failure? | Yes | No | 1,0 | 340 |
| 312 | Infection? | Yes | No | 0,1 | 342 |

Treatment administration data 106

| # | Field | | | | Vector | # |
|---|---|---|---|---|---|---|
| 314 | Hospital admission type | Regular | Urgent care | Emergency | 0,1,0 | 344 |
| 316 | Insurance source | Public insurance | Private insurance | | 0,1 | 346 |
| 318 | Hospital operator | Z number of alternatives | | | 0,...1,...0000 | 348 |
| 320 | Hospital type | Teaching hospital | Non-teaching hospital | | 0,1 | 350 |
| 322 | Hospital bed numbers | <99 | 100-500 | >500 | 0,0,1 | 352 |
| 324 | Point of referal | Health care provider | Non health care provider | | 1,0 | 354 |

Patient features vector 301

FIG. 3A

Demographic data 204

| # | Field | | | | Cluster features vector 305 | |
|---|---|---|---|---|---|---|
| 300 | Age Group | 18-44 | 45-64 | 65-74 | >74 | 0.3, 0.1, 0.5, 0.1 — 360 |
| 302 | Marital status | Single | Married | | Other | 0.3, 0.4, 0.3 — 362 |
| 304 | Race | X number of alternatives | | | | 0.1, . . . 0.5, . . . 0, 0 — 364 |
| 306 | Gender | Male | Female | | Other | 0.9, 0.1, 0 — 366 |
| 308 | Locale | Y number of alternatives | | | | 0.1, . . . 0.5, . . . 0, 0 — 368 |

Diagnostic data 206

| # | Field | | | |
|---|---|---|---|---|
| 310 | Organ failure? | Yes | No | 0.9, 0.1 — 370 |
| 312 | Infection? | Yes | No | 0.9, 0.1 — 372 |

Treatment administration data 106

| # | Field | | | | |
|---|---|---|---|---|---|
| 314 | Hospital admission type | Regular | Urgent care | Emergency | 0.5, 0.4, 0.1 — 374 |
| 316 | Insurance source | Public insurance | Private insurance | | 0.2, 0.8 — 376 |
| 318 | Hospital operator | Z number of alternatives | | | 0.1, . . . 0.5, . . . 0, 0 — 378 |
| 320 | Hospital type | Teaching hospital | Non-teaching hospital | | 0.2, 0.8 — 380 |
| 322 | Hospital bed numbers | <99 | 100-500 | >500 | 0.2, 0.4, 0.2 — 382 |
| 324 | Point of referal | Trauma center | Family doctor | | 0.9, 0.1 — 384 |

FIG. 3B

MEDICAL TREATMENT METRIC MODELLING BASED ON MACHINE LEARNING

CROSS-REFERENCES TO RELATED APPLICATIONS

The present application claims benefit of priority to U.S. Provisional Patent Application No. 62/766,985, filed Nov. 12, 2018, the content of which is herein incorporated by reference in its entirety for all purposes.

BACKGROUND

A disease can bring a lot of suffering to a patient, especially for diseases that can bring upon substantial morbidity, mortality, as well as economic burden to the patient, such as sepsis and cancer. Yet, little is known about how to identify which action among many options will actually improve the quality of care and reduce the economic burden on the patients. For example, there can be hidden biases that influence the length of hospitalization, the administration of treatment, etc., and the biases can be unrelated to the severity of the disease or the quality of care provided to the patients. Those hidden biases can be related to certain personal attributes of the patients (e.g., demography, locale, etc.). Currently, there lacks a way to accurately identify actions that influence the quality and effectiveness of care to improve clinical decisions and medical resource managements.

BRIEF SUMMARY

Disclosed herein are techniques for performing segment analysis of patient data to improve clinical decision making and medical resource management. The clinical decision making may include, for example, choosing/recommending a hospital to administer the treatment to a patient, determining a length of hospitalization (LOH) of the patient, etc. The medical resource management may include, for example, changing the operations at a hospital in administering a treatment to patients of a certain disease, reducing the LOH of the patients who share certain personal attributes, etc.

In some embodiments, the techniques include obtaining patients data of a plurality of patients. The patients may have contracted a common illness (e.g., sepsis), have received medical treatments for the illness, and have since recovered. The patients data of each patient may include, for example, characteristics data for each patient, administration data related to the treatment each patient has received, treatment metrics data related to the medical treatments, etc. The characteristics data, the administration data, and the treatment metrics data may each be associated with a plurality of data categories. The characteristics data may include different categories of data including, for example, demographic data (which may include categories such as age, gender, race, etc.), locale (which may include categories such as city of residence, urban or rural area, etc.), the diagnosis results of the patient before and/or during the medical treatment, etc. The diagnosis results may be specific to the illness and may include categories of data indicating, for example, whether the patient suffered from an organ failure, whether the patient has contracted an inflection, etc. Moreover, the administration data may include categories of data identifying, for example, the hospital where the patient stayed for the medical treatment, whether the hospital is a teaching hospital or non-teaching hospital, a number of inpatient beds of the hospital, insurance provider information, etc. The treatment metrics data may include, for example, a length of hospitalization (LOH) of the patient for the medical treatment, cost, and other metrics to evaluate the quality of the medical treatment (e.g., recurrence of the illness, etc.).

The characteristics data and the administration data of each patient can be used to compute a patient features vector for the patient. A patient features vector of a patient may represent a plurality of features, with each feature indicating values of the patient data in the plurality of data categories including, for example, a category of the characteristics data of a patient, a category of administration data of the patient, etc. For example, the age of a patient can be a feature represented in a patient features vector, whereas the hospital where the patient stayed for the treatment can be another feature represented in the patient features vector.

Unsupervised machine learning techniques can be used to divide the patient features vectors into segments or clusters. Specifically, a two-stage clustering process can be performed on the patient features vectors. Patient features vectors of the plurality of patients can be clustered into a first set of first clusters based on, for example, cosine distance clustering, and a cluster features vector can be computed for each cluster of the first set of first clusters. A cluster features vector may be computed for each first cluster to represent a distribution of each for each of the plurality of data categories in the first cluster. The cluster features vectors, which represent the first set of first clusters of patient characteristics data and treatment administration data, can be further clustered into a second set of second clusters based on, for example, Euclidean distance clustering (e.g., K-means clustering). Each second cluster of the second set of second clusters can include a subset of the first set of first clusters represented by the cluster features vectors, and each cluster feature vector itself can represent a cluster of patients in the first set of first clusters. Through the two-stage clustering, the patients data can be divided into clusters according to the clustering of the cluster features vectors.

The patients data in each second cluster can be further processed based on supervised machine learning techniques to determine a relationship between each patient feature (e.g., age, gender, which hospital the patient stayed, etc.), represented by the patient features vectors, and each of the treatment metrics (e.g., length of hospitalization, cost, recurrence, etc.). The supervised machine learning techniques may include, for example, partial least square regression (PLSR), linear regression, etc. Various models can be determined. In some examples, a model representing the relationships between the patient features values and the treatment metrics values can be determined. In some examples, based on the relationships, a model representing influences exerted by each patient feature on a treatment metric can be determined for each cluster. For example, treatment metric values for patients having a particular patient feature (e.g., being part of an age group) and treatment metric values for patients not having that patient feature (e.g., not part of the age group) can be determined. Based on the differences between these treatment metric values, the effect of absence or presence of that patient feature on the treatment metric category can be determined. Other techniques, such as Variables Importance on Partial Least Squares (PLS) projections (VIP), can also be employed. The model may also include, for example, a ranking of the patient features according to their degrees of influence.

The model can be used to assist in generating a clinical decision. In one example, a new patient is accepted at a hospital, and a decision is to be made about selecting a treatment to be provided to the new patient (e.g., length of hospitalization, whether the new patient should be transferred to another hospital, etc.) out of a plurality of clinical options. The new patient may have a set of patient features comprising the characteristics data, as well as an incomplete set of administrative data in which features corresponding to the clinical options to be determined are missing. A treatment metric model can be identified for the new patient based on the models and clusters created from the aforementioned two-stage clustering process. Specifically, the new patient can be classified into one of the clusters of patients based on comparing the characteristics data of the new patient with the characteristics data of patients of each cluster, and a model representing the relationships between the patient features values (which include the characteristics data and administrative data) and the treatment metrics values for that one cluster can be identified. Different sets of administrative data representing different clinical options can be combined with the characteristics data of the new patient to generate a set of inputs to the model, and different treatment metric values can be computed for the set of inputs. A clinical option that gives rise to an optimal treatment metric (e.g., shortest LOH) can then be selected for the new patient. As an illustrative example, if the treatment metric output of the model indicates that transferring the new patient to another hospital can lead to a shorter length of hospitalization, a decision can be made to transfer to new patient to another hospital.

As another example, a model of influences of patient features on a treatment metric specific for that one cluster can also be identified. If the new patient has features matching the highest ranked features in the model, the clinical decision can be made based on the influences of those features. As an illustrative example, the model may indicate that being part of a particular age group has a large and positive influence on the length of hospital stay, which may suggest that patients in that age group tends to stay in the hospital longer to recover. If the new patient is also in that age group, a decision can be made to extend the length of hospitalization for the new patient. As another example, the model may also indicate that staying in a non-teaching hospital has a large and negative influence on the length of hospitalization. In such a case, a decision can be made to transfer the new patient to a non-training hospital to reduce the length of hospitalization for the patient, which can also reduce the economic burden on the patient.

The model can also be used to improve medical resource management by, for example, identifying administrative factors that impact the treatment metrics but are unrelated to the severity of the illness. For example, for a cluster of patients, the model may indicate that staying at a specific hospital has a large and positive influence on the length of hospitalization at that hospital, while the severity of the illness has a relatively small impact on the length of hospitalization at that hospital. Based on this indication, inquiries specific to that hospital can be made to determine the causes for the longer length of hospitalization, and to determine which action (e.g., more training, more equipment, etc.) can be undertaken to shorten the length of hospitalization for the patients there.

The two-stage clustering techniques can reduce the computation time and resource needed to generate the treatment metric model. Specifically, performing a regression analysis directly on a large volume of patients data can be very computation-intensive. In contrast, the two-stage clustering provides a divide-and-conquer approach where the patients data having certain degree of similarities are divided into clusters, and then a treatment metric model is created for each cluster. As the volume of patients data involved in creation of each treatment metric model is reduced, the computation resource and time required for the creation of the metric model can be reduced.

In addition, the two-stage clustering process can also generate a discriminative set of clusters using reduced computation time and resource. Specifically, the patients data can be encoded into patients features vectors using one-hot encoding scheme to become more compact and require fewer computation time and resource for processing. Cosine distance clustering can be performed on the one-hot encoded patients features vectors to generate a first set of first clusters. A cluster features vector may be computed for each cluster of the first set of first clusters to represent a distribution of each of the plurality of features in the cluster, and K-means clustering (based on Euclidean distance) can be performed on the cluster features vectors to generate a second set of second clusters. While K-means clustering typically can provide a more discriminative set of clusters, applying K-means clustering directly on all the patients data can also be very computation-intensive. With the two-stage clustering process, K-means clustering is performed on the cluster features vectors (which represents the patients data in a condensed form) with reduced computation resource and time. The two-stage clustering process also allow more patients data to be included in the clustering process and the subsequent treatment metric model generation, which can further improve the treatment metric models as well as the clinical decisions made based on these models.

These and other embodiments of the invention are described in detail below. For example, other embodiments are directed to systems, devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

The detailed description is set forth with reference to the accompanying figures.

FIG. 3A-FIG. 3D illustrate an example of a two-stage clustering process to divide patients data into clusters, according to certain aspects of this disclosure.

DETAILED DESCRIPTION

Figure 1:
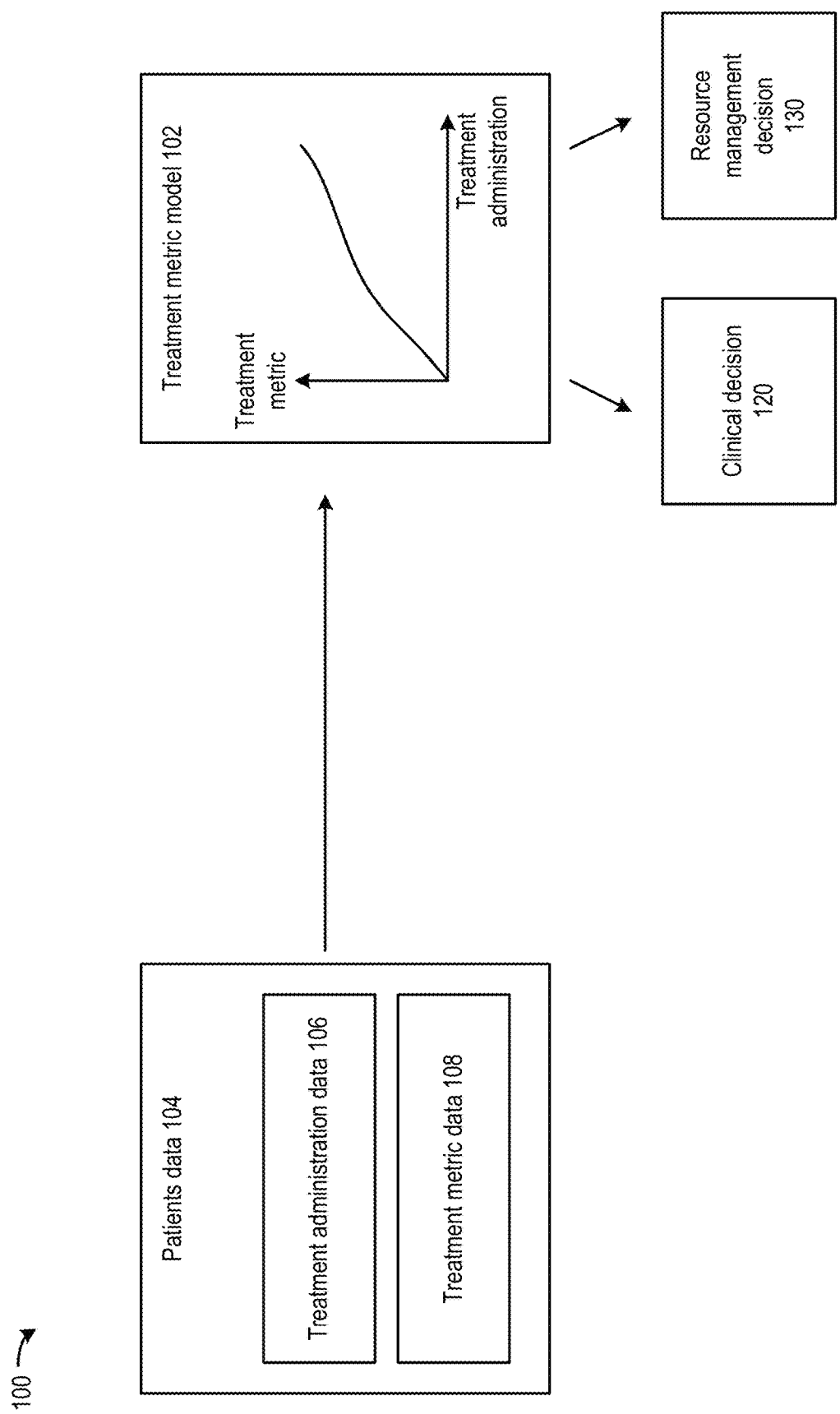
FIG. 1 is an example flow diagram for determining a treatment metric model.

Disclosed herein are techniques for performing segment analysis of patients data to identify relationships between different characteristics of the patients data and treatment metrics. A model of influences of the different categories of the patients data on the treatment metrics can be created. The model can be used for various applications such as, for example, improving clinical decision making, medical resource management, etc.

More specifically, patient data of a plurality of patients can be obtained. The patients may have contracted a common illness (e.g., sepsis), have received medical treatments for the illness, and have since recovered. The patient data of each patient may include characteristics data and treatment administration data of the each patient, as well as metrics data related to the medical treatments. The characteristics data and the treatment administration data may be associated with a plurality of categories including, for example, demographic data, locale, the diagnosis results of the patient, medical provider information, etc. The metrics data may include, for example, a length of hospitalization (LOH) of the patient for the medical treatment, cost, and other metrics to evaluate the quality of the medical treatment (e.g., recurrence of the illness, etc.).

The characteristics data and the treatment administration data of each patient can be used to compute a patient features vector for the patient. A patient features vector of a patient may represent a plurality of features, with each feature corresponding to a category of data of the characteristics data and treatment administration data of a patient. The patient features vectors of the plurality of patients can be computed from the patient data. Unsupervised machine learning techniques can be applied to divide the patient features vectors into clusters. For example, a two-stage clustering processing can be performed on the patient features vectors. Specifically, the patient features vectors can be clustered into a first set of first clusters. A cluster features vector may be computed for each first cluster of the first set of first clusters to represent a distribution for each of the plurality of data categories. The cluster features vectors, which represent the first set of first clusters of patient characteristics data and treatment administration data, can be further clustered into a second set of second clusters. Through the two-stage clustering, the patient data can be clustered into the second set of second clusters.

The patient data in each second cluster of the second set of second clusters can be further processed using supervised machine learning techniques, such as regression, to determine a treatment metric model representing a relationship between each patient feature and the treatment metrics. The treatment metric model can be used to, for example, process second patient data of a new patient to generate a clinical decision for the new patient (e.g., length of hospitalization, which hospital to receive the treatment, etc.), to perform medical resource management to improve the treatment metrics, etc.

The two-stage clustering techniques can reduce the computation time and resource needed to generate the treatment metric model. Specifically, performing a regression analysis directly on a large volume of patients data can be very computation-intensive. In contrast, the two-stage clustering provides a divide-and-conquer approach where the patients data having certain degree of similarities are divided into clusters, and then a treatment metric model is created for each cluster. As the volume of patients data involved in creation of each treatment metric model is reduced, the computation resource and time required for the creation of the metric model can be reduced.

In addition, the two-stage clustering process can also generate a discriminative set of clusters using reduced computation time and resource. Specifically, the patients data can be encoded into patients features vectors using one-hot encoding scheme to become more compact and require fewer computation time and resource for processing. Cosine distance clustering can be performed on the one-hot encoded patients features vectors to generate a first set of first clusters. A cluster features vector may be computed for each cluster of the first set of first clusters to represent a distribution for each of the data categories in the cluster, and K-means clustering (based on Euclidean distance) can be performed on the cluster features vectors to generate a second set of second clusters. While K-means clustering typically can provide a more discriminative set of clusters, applying K-means clustering directly on all the patients data can also be very computation-intensive. With the two-stage clustering process, K-means clustering is performed on the cluster features vectors (which represents the patients data in a condensed form) with reduced computation resource and time. The two-stage clustering process also allow more patients data to be included in the clustering process and the subsequent treatment metric model generation, which can further improve the treatment metric models as well as the clinical decisions made based on these models.

I. Treatment Metric Modelling Based on Segment Analysis of Patient Data

Figure 2:
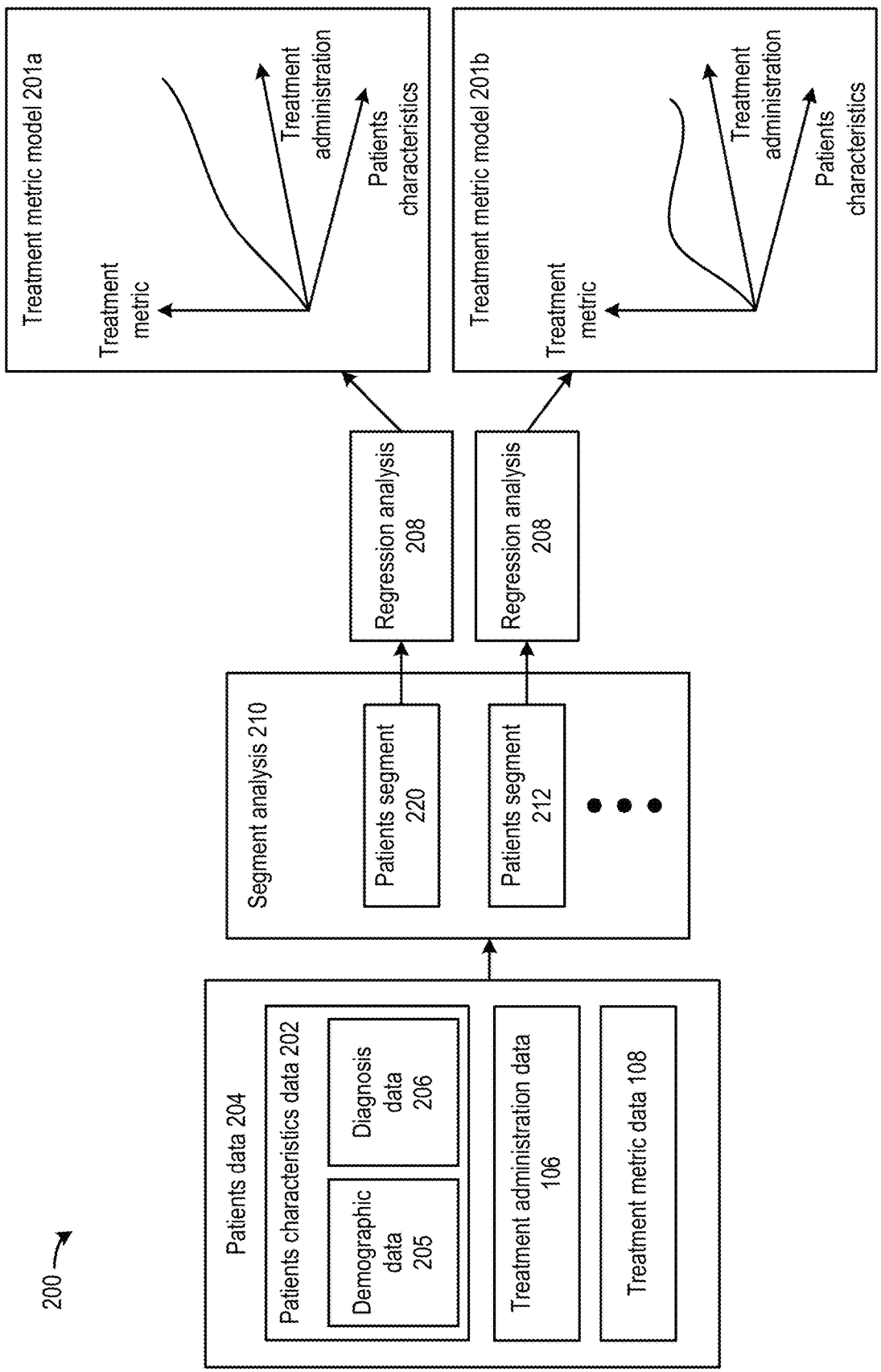
FIG. 2 illustrates an improved method of determining a treatment metric model.

FIG. 1 is an example flow diagram 100 of a method for generating treatment metrics to support a clinical and/or resource management decision, whereas FIG. 2 illustrates a flow diagram 200 of an improved method for generating the treatment metrics for the decisions. A treatment metric model can be used to predict a treatment metric for a particular administration of a treatment. Treatment metrics can measure various aspects of the medical treatments received by patients for an illness, such as length of hospitalization (LOH), recurrence of the illness, cost, etc. A treatment metric for an illness may be impacted by various factors, such as the treatment method, the provider of the treatment, etc. In FIG. 1, treatment metric model 102 may define relationships that quantify the impacts of these factors on a treatment metric. To generate treatment metric model 102, such as a model that defines length of hospitalization (LOH), cost, etc. for a sepsis patient, patients data 104 of patients who have received a treatment for sepsis can be collected.

Patients data 104 may include treatment administration data 106, which may include information about prior treatment decisions including, for example, the treatments the patients have received, the providers of those treatments, etc. Patients data 104 may also include treatment metric data 108 (e.g., length of hospitalization, cost, etc.) for those treatments. A relationship between treatment administration data 106 and treatment metric data 108 can be determined. Treatment metric model 102 can model the impacts of various treatment decisions (as reflected in treatment administration data 106) on treatment metric data 108 based on the relationship.

Treatment metric model 102 can be used to support different applications to improve the quality of care and reduce economic burden on the patients, such as supporting a clinical decision 120 for a new patient, supporting a resource management decision 130, etc. For example, a clinical decision 120 can be made to select (and provide) a treatment method for the new patient, to select a provider of the treatment, etc. The decision can be driven by a treatment metric of the treatment and/or the provider using treatment metric model 102. For example, a treatment method provided by a specific provider can be selected based on the treatment metrics (e.g., low LOH, low cost, etc.) of the treatment method and the provider according to treatment metric model 102.

A resource management decision 130 can be made to determine what resource is to be allocated to a provider of treatment, and the determination can be driven by a treatment metric of the provider provided by treatment metric model 102. For example, if the provider has a much worse metric (e.g., a longer LOH, a higher cost, etc.) than other providers when providing a treatment method according to the metric, resources can be allocated to that provider (e.g., to improve training of the staff) to improve its operations in providing the treatment method.

Although treatment metric model 102 can provide insight into certain factors related to the treatment history, treatment metric model 102 does not take into account other factors, such as patients characteristics, which can affect the relevancy of treatment metric model 102 to individual patients for clinical decision making. For example, the demographic data of a patient (e.g., age, gender, race, locale, etc.), as well as diagnosis data of the patient prior to and during the treatments, may also affect the treatment metric for that patient. As an illustrative example, patients in different age groups, having different initial diagnoses, etc., may have different responses to the same medical treatment provided by the same provider, which can lead to different treatment metrics for the patients (e.g., different LOH, different costs, etc.). In addition, there can be hidden factors that influence the length of hospitalization, the choice and location of treatment, etc. and the biases are unrelated to the severity of the disease or the quality of care provided to the patients but can be related to other patient characteristics. A clinical decision made without taking into account the patients characteristics and these hidden factors can degrade the treatment metric for the treatment, as well as the quality of care, provided to the patients. Moreover, a resource management decision that fails to take into account these hidden factors can also lead to inefficient utilization of resources without improving the quality of care provided to the patients.

FIG. 2 illustrates flow diagram 200 of an improved method for generating treatment metrics to support a clinical and/or resource management decision. As shown in FIG. 2, a plurality of treatment metric models 201, including treatment metric model 201a and 201b, can be determined from patients data 204. As shown in FIG. 2, patients data 204 include, in addition to treatment administration data 106 and treatment metric data 108, patients characteristics data 202. Patients characteristics data 202 can include various characteristics data of the patients including, for example, demographic data 205 and diagnosis data 206 of the patients.

Patients data 204 can be processed using supervised machine learning techniques to determine the relationships between a treatment metric (e.g., LOH) and various treatment decisions and patients characteristics. One example of supervised machine learning techniques may include regression analysis 208, such as partial least square regression (PLSR), linear regression, etc. In data regression, the known associations among the treatment metrics data set, the treatment decisions data set, and patients' characteristics data set, as reflected in patients data 204, can be considered ground truth. Through an interactive data regression process, a function describing a relationship among the treatment metrics, the treatment decisions, and patients characteristics that fits (within certain tolerance) among the known associations between the data sets can be determined.

Although regression analysis 208 can be performed on patients data 204 directly, such an approach can be very computation-intensive especially when patients data 204 comprise data of a large patient population, which can result in a large and diverse set of patients characteristics data 202. Specifically, the interactive data regression process may involve determining and adjusting the model parameters to fit the patients data. The computation time and resource involved can become prohibitively large as more patients data are used to determine the treatment metric model. On the other hand, maximizing the amount of patients data involved in the regression analysis allows the treatment metric model to cover more associations among the treatment metrics data set, the treatment decisions data set, and patients' characteristics data set, so that the treatment metric model is more likely to generate a metric that is relevant to a patient.

To reduce the computation time/resource involved in the regression analysis, the patients can be divided into different patient clusters or segments, and then a regression analysis can be performed on the patients data for each cluster of patients to generate a treatment metric model. A new patient can then be classified into one of the patient cluster, and the treatment metric model of that cluster can be used to determine the treatment metrics for the new patient.

Specifically, referring to FIG. 2, a segment analysis 210 can be performed on patients characteristics data 202 and treatment administration data 106 to divide the data (and the patients represented by the data) into clusters that exhibits a certain degree of similarity. The division of patients data 204 into clusters can reduce the volume and non-uniformity of data to be processed by regression analysis 208, both of which can reduce the complexity of the regression analysis. Regression analysis 208 can be performed on each segment of patients data 204 to determine a treatment metric model associated with the segment. For example, treatment metric model 201a can be determined from segment 210 of patients data 204, whereas treatment metric model 201b can be determined from segment 212 of patients data 204. One treatment metric model can be selected from treatment metric models 201a or 201b to generate a clinical decision for a new patient, a medical resource management decision for a hospital, etc., based on matching the characteristics of the new patient and/or the hospital with the segments of patients characteristics data 202 and treatment administration data 106.

II. A Two-Stage Clustering Process

There are various challenges associated with performing segment analysis on a large volume of patients data 204. For example, supervised learning techniques are unsuitable for segment analysis 208, given that very little is known about the similarities (or differences) among patients characteristics data 202 and treatment administration data 106 of each patient. Further, there is no ground truth that can be relied upon as criteria for dividing patients data 204. Therefore, unsupervised learning techniques, such as clustering, may be employed to learn (e.g., measure) the similarities among patients characteristics data 202 and treatment administration data 106 of each patient, and to group the patients according to the similarity measurements into clusters. One big challenge with clustering is to determine a metric for the similarity measurements such that the measurements can reflect the proper differences and similarities among patients characteristics data 202 and treatment administration data 106 of each patient.

Figure 3C:
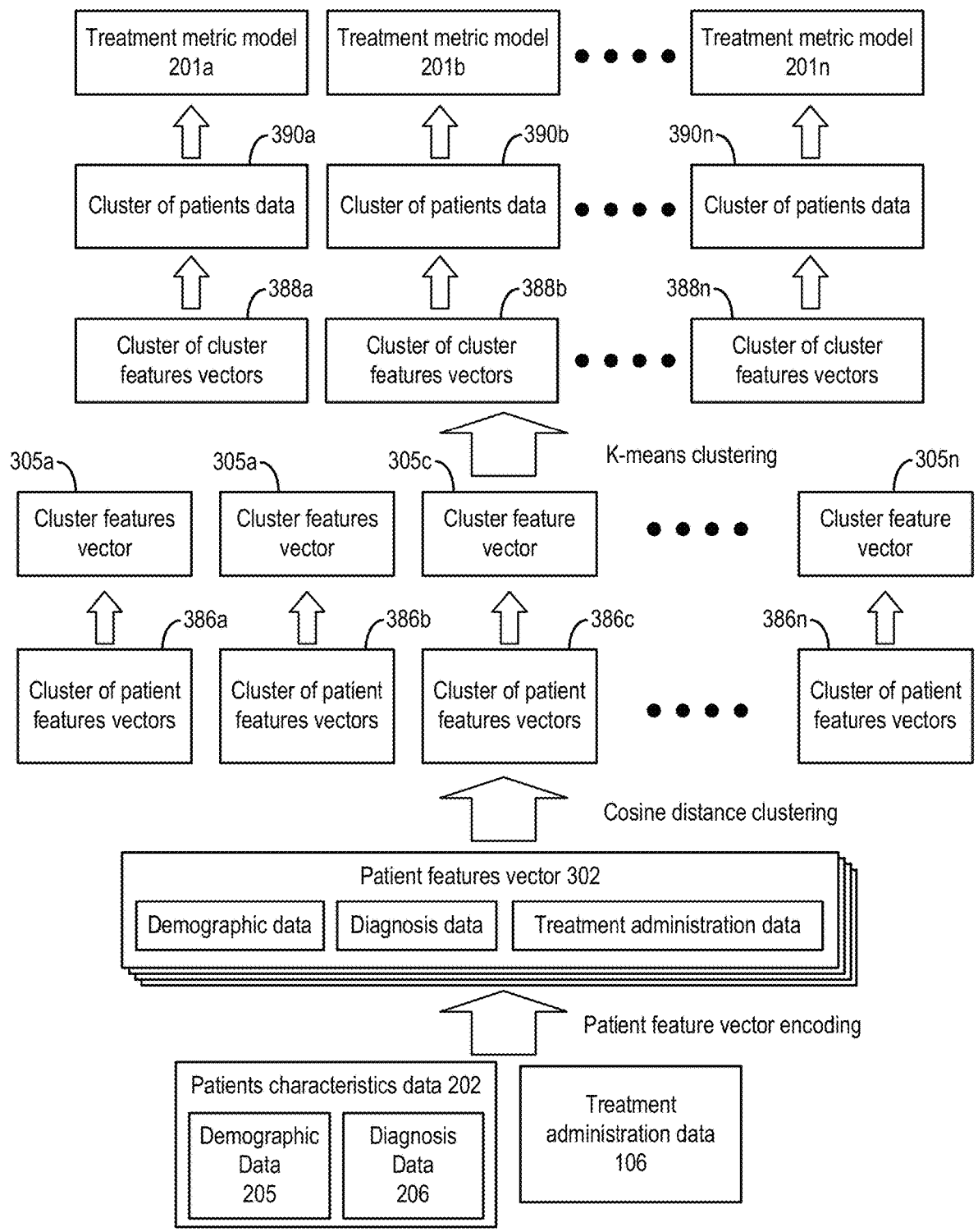
Figure 3D:
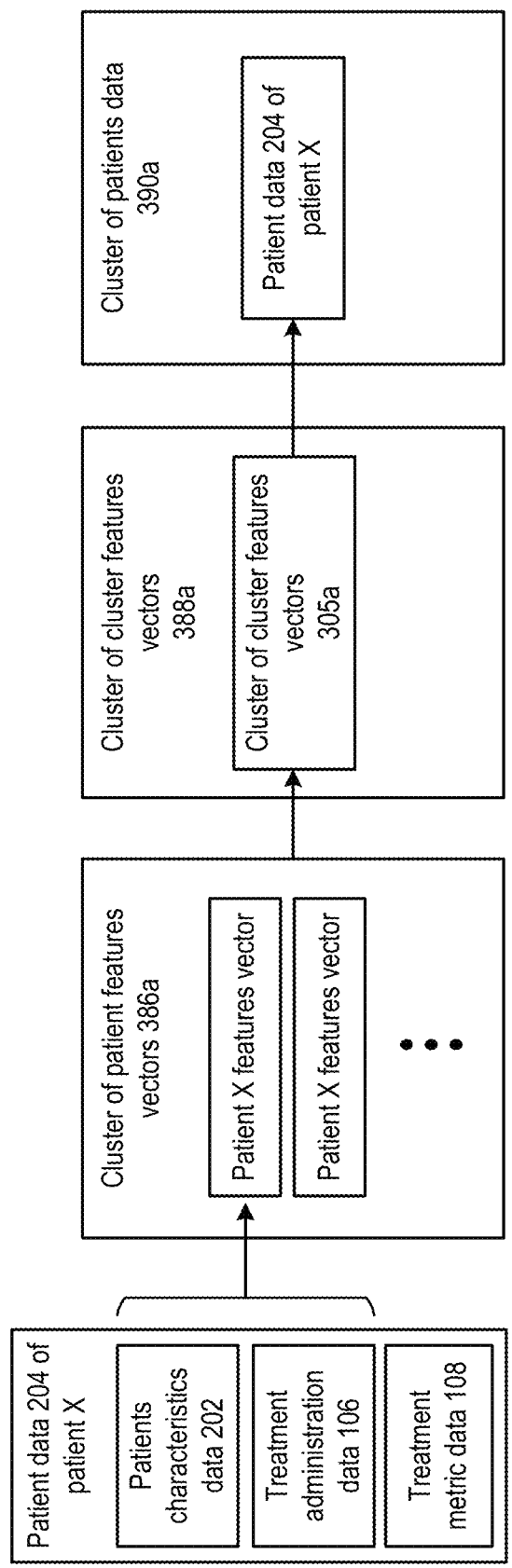

FIGS. 3A-3D illustrate an example of a two-stage clustering process to divide patients data into clusters. The two-stage clustering process includes clustering patient features vectors into a first set of first clusters. A cluster features vector may be computed for each of the first set of first clusters to represent, for example, a distribution for each of the plurality of data categories in the cluster. The cluster features vectors can be further clustered into a second set of second clusters. Through the two-stage clustering, the patients of whom the patients data are clustered can be divided into clusters. As to be described below, FIG. 3A illustrates examples of patent features vectors representing patients data 204, FIG. 3B illustrates an example of cluster features vectors, whereas FIG. 3C illustrates an example of a two-stage clustering process which is performed based on the example patent features vectors of FIG. 3A and which generates the example cluster features vectors of FIG. 3B. FIG. 3D illustrates a mapping process to cluster the patients based on the second set of second clusters.

A. Examples of Patient Features Vectors

FIG. 3A illustrates an example of a patient features vector 301 of a patient and its mapping to demographic data 205, diagnosis data 206, and treatment administration data 106 of the same patient. As shown in FIG. 3A, each of demographic data 205, diagnosis data 206, and treatment administration data 106 includes a plurality of categories of data, with each category assigned a value for the patient. For example, the data categories of demographic data 205 may include different demographic information of the patient including age group 300, marital status 302, race 304, gender 306, and locale 308 of the patient. Moreover, the data categories of diagnostic data are related to various potential diagnoses of the patient before or during a treatment and may include organ failure 310 and infection 312. Further, the data categories of treatment administration data 106 include various information about the administration of the treatment to the patient and may include hospital admission type 314, insurance source 316, hospital operator 318, hospital type 320, hospital bed numbers 322, and point of referral 324.

Each data category of demographic data 205, diagnosis data 206, and treatment administration data 106 can be mapped to a feature of patient features vector 301. A feature of patient features vector 301 can correspond to a data category, and the value of the data category (represented by the grey box) can be encoded into a feature value. For example, feature 330 corresponds to age group 300, feature 332 corresponds to marital status 302, feature 334 corresponds to race 304, feature 336 corresponds to gender 306, feature 338 corresponds to locale 308, feature 340 corresponds to organ failure 310, feature 342 corresponds to infection 312, feature 344 corresponds to hospital admission type 314, feature 346 corresponds to insurance source 316, feature 348 corresponds to hospital operator 318, feature 350 corresponds to hospital type 320, feature 352 corresponds to hospital bed numbers 322, whereas features 354 corresponds to point of referral 324.

In some embodiments, a one-hot encoding scheme can be employed to encode a value of data category into a feature. A data category can have a set of alternative values, and the value of the data category can be indicated by the selection of one of the alternative values. A feature can have a set of bits corresponding to the set of alternative values, and one of the bits can be set to indicate the value selected for the data category. For example, referring to FIG. 3B, age group 320 can be one of a first age group between the ages of 18-44, a second age group between the ages of 45-64, a third age group between the ages of 65-74, and a third age group beyond the age of 74. Feature 350, which corresponds to age group 320, can have four bits representing the four alternative age groups for age group 320, and one of the bits can be set to represent which of the four alternative age groups the patient belongs to. In the example of FIG. 3B, the patient is in the first age group 18-44 (as represented by the shading of the first age group), and the first bit of feature 350 is set. The bits in other features are also set according to which alternative values are selected for other data categories (as represented by the shading).

As part of the two-stage clustering process, patient feature vectors 301 clinical decision generator can be clustered into a first set of first clusters based on a similarity metric. The one-hot encoding scheme allows patients data to be represented in a binary format, which allows the patient features vector to become more compact and requires fewer computation resources for the clustering operation. However, the binary representation can impose limit on the similarity measurements for clustering operation. For example, since with one-hot encoding, each feature always have one bit set to one and the rest of the bits set to zero, a Euclidian distance between two different feature values can be always one. As a result, Euclidian distance cannot accurately measure a degree of similarity (or difference) between two one-hot encoded vectors.

On the other hand, cosine distance, which is generated by the inner product between two vectors and represent an angle formed by the two vectors, can provide a more accurate measurement of a degree of similarity between two one-hot encoded patient features vectors. But the cosine distance measurement between binary representations of patient features vectors only reflects the difference in angles, while ignoring the magnitudes of the patient features which can also indicate a degree of similarities. As a result, a clustering operation based on cosine distances between binary representations of feature vectors may generate a large number of small clusters, yet the clusters are not sufficiently different from one another, and there is insufficient discrimination among the clusters. Moreover, with each cluster only representing a very small population of the patients, the patient characteristics data 202 and treatment administration data 106 in each cluster, as well as the corresponding treatment metric data 108, may be unable to provide sufficient insight of the relationship among these data and may be unsuitable for treatment metric model generation.

B. Examples of Cluster Features Vector

To improve the discrimination among the first set clusters, as part of the two-stage clustering process, the first set of first clusters of patient features vectors can be further clustered into a second set of second clusters. Specifically, for each of the first set of first clusters, a cluster features vector can be computed to provide a numerical representation of the features represented by the patient features vectors in the cluster. Each feature in a cluster features vector can represent a feature in patient features vector. Each feature in cluster features vector 305 can include a number representing a distribution of the alternative values for each data category in the patient features vectors of a cluster of the first set of first clusters.

For example, as described above, a feature in a patient cluster vector can be represented by a set of bits, with each bit corresponding to an alternative value for the corresponding data category. A feature in a cluster features vector of a cluster can have a set of numerical values corresponding to the set of alternative values of the corresponding feature in the patient features vectors of the clusters. Each numerical value of a feature of the cluster features vector can represent a percentage of occurrence of that alternative value for the corresponding data category within that cluster, such that each feature in cluster features vector can represent a distribution of the alternative values within the cluster.

FIG. 3B illustrates an example of a cluster features vector 305 computed for a cluster of the first set of first clusters. As shown in FIG. 3B, cluster features vector 305 also include features 360-384 mapped to the data categories of demographic data 205, diagnosis data 206, and treatment administration data 106, as described above. Each feature of cluster features vector 305 can represent a distribution of the alternative values for a corresponding data category among the patient features vectors 301 of the cluster. For example, feature 360, corresponding to age group 300, can indicate that within a cluster, 30% (represented by 0.3) of the patients are of the first age group 18-44, 10% of the patients are of the second age group 45-64, 50% of the patients are of the third age group 65-74, and 10% of the patients are of the fourth age group beyond the age of 74. Likewise, feature 370, corresponding to organ failure 330, can indicate that within the cluster, 90% of the patients experienced organ failure and 10% of the patients have not experienced organ failure. With such arrangements, a cluster features vector 305 can include a numerical representation, or a numerical sample, of the features of a group of patients who exhibit certain degree of similarity in terms of demographic, diagnostic results, and treatment administration.

The cluster features vectors 305 can be clustered using K-means clustering based on computation of Euclidean distances between the cluster features vectors to generate a second set of second clusters, with each cluster of the second set of second clusters including a subset of the first set of first clusters. Euclidean distance computation are suitable because, unlike patient features vectors 301 which are one-hot encoded and only carry binary values (ones or zeros), each cluster features vector 305 includes a numerical representation of the features. The numerical representation can be any number within a range and is not binary. A degree of similarity (or difference) between two cluster features vectors 305 can be reflected from the Euclidean distance computed from the numerical representations of the features of the vectors.

The clustering of cluster features vectors based on Euclidean distance, as part of the two-stage clustering operation, provides several advantages. For example, since the Euclidean distance is based on the magnitudes of each feature of the vectors, the Euclidean distance can provide a more accurate measurement of the degree of similarity (and difference) among the vectors, which allows the second set of second clusters to be have more discrimination among the clusters. Moreover, with each cluster only representing a larger population of the patients, the patient characteristics data 202 and treatment administration data 106 of the patients represented in each cluster, as well as the corresponding treatment metric data 108, can provide more insight of the relationship among these data and can be used to create treatment metric models that can provide a more accurate prediction of a treatment metric.

Moreover, as k-means clustering is performed only on the cluster features vectors which are much fewer than the number of patient features vectors, the computation time and resource needed for the clustering can be reduced compared with, for example, applying K-means clustering on patients feature vectors that include numerical representations rather than binary representation of the features. This also allows more patients data to be included in the clustering operation to further improve the treatment metric models.

C. Examples of Two Stage Clustering

FIG. 3C illustrates an example of a two stage clustering operation based on patients characteristics data 202. As shown in FIG. 3C, patients characteristics data 202 and treatment administration data 106 of each patient can first be encoded into patient features vectors 301, the details of which are described in FIG. 3A. Patient features vectors 301 can be clustered into a first set of first clusters (of patient features vectors 301) including, for example, cluster 386a, cluster 386b, cluster 386c, cluster 386n, etc. The clustering of patient features vectors 301 can be performed based on cosine distance clustering techniques as described above.

Moreover, cluster features vector 305, including cluster features vector 305a, cluster feature vectors 305b, cluster feature vector 305c, cluster feature vector 305n, etc., can be determined for, respectively, cluster 386a, cluster 386b, cluster 386c, and cluster 386n, to represent a distribution of the alternative values of each feature among the patient features vectors 301 in the respective cluster. For example, a cluster features vector 305a can be determined for cluster 304a, cluster features vector 305b can be determined for cluster 304b, cluster features vector 305c can be determined for cluster 304c, cluster features vector 305n can be determined for cluster 304n, etc. The details of cluster features vectors 305 are described in FIG. 3B.

Cluster features vectors 305 (e.g., cluster features vectors 305a, 305b, 305c, 305n, etc.) can be clustered into a second set of second clusters 388 including, for example, cluster 388a, cluster 388b, cluster 388n, etc. The clustering of cluster features vectors 305 can be performed based on K-means clustering techniques as described above. Each cluster of clusters 388 can include a plurality of cluster features vectors 305, which can represent a subset of first set of first clusters 386.

After the second set of second clusters 388 (of cluster features vectors 305) are formed, patients data 204 of each patient, including patients characteristics data 202 and treatment administration data 106, can be clustered into clusters 390 of patients data including, for example, patients data cluster 390a, patients data cluster 390b, patients data cluster 390n, etc., based on the second set of second clusters 388. Specifically, referring to FIG. 3D, the patients data 204 of each patient (e.g., patient X) can be mapped to a patient features vector 301 (e.g., "patient X features vector" in FIG. 3D) included in the first set of first clusters 386a. Patients data 204 include patients characteristics data 202 and treatment administration data 106 which are encoded in the patient features vectors 301, as well as treatment metrics data 108. As first set of first clusters 386a is represented by a cluster features vector 305 (e.g., cluster features vector 305a) in one of the second set of second clusters 388 (e.g., cluster 388a), through the mapping between cluster features vector 305a and cluster 388a, patient X data can be clustered in a cluster 390a of patients data which corresponds to cluster 388a. Other patients data clusters, such as cluster 390b, cluster 390n, etc., can also be formed. The cluster of patients data can then be submitted to regression analysis 208 to generate treatment metric models 201 including, for example, treatment metric model 201a, treatment metric model 201b, treatment metric model 201c, as described above. For example, treatment metric model 201a can be generated from patients data cluster 390a, treatment metric model 201b can be generated from patients data cluster 390b, treatment metric model 201c can be generated from patients data cluster 390c, etc.

III. Supervised Machine Learning Processing of Patients Data Clusters

The patient data in each segment can be further processed based on supervised machine learning techniques to determine a relationship between a patient feature (e.g., age, gender, which hospital the patient stayed, etc.) and a treatment metric (e.g., length of hospitalization, cost, recurrence, etc.), to determine a treatment metric model for that segment. The supervised machine learning techniques may include, for example, partial least square regression (PLSR), linear regression, etc.

Figure 4A:
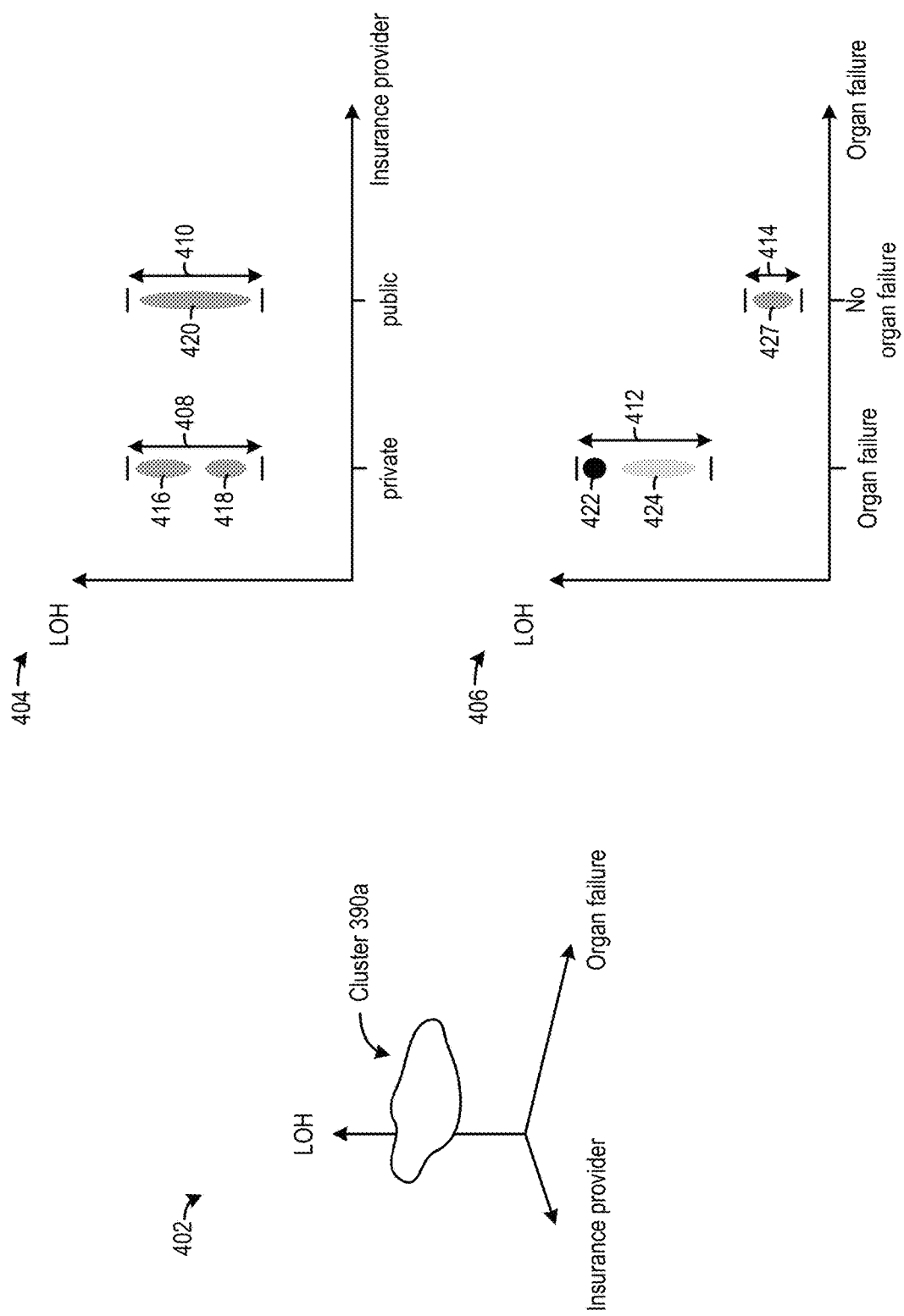
FIG. 4A-FIG. 4C illustrate examples of supervised machine learning techniques to generate a treatment metric model, according to certain aspects of this disclosure.
Figure 4B:
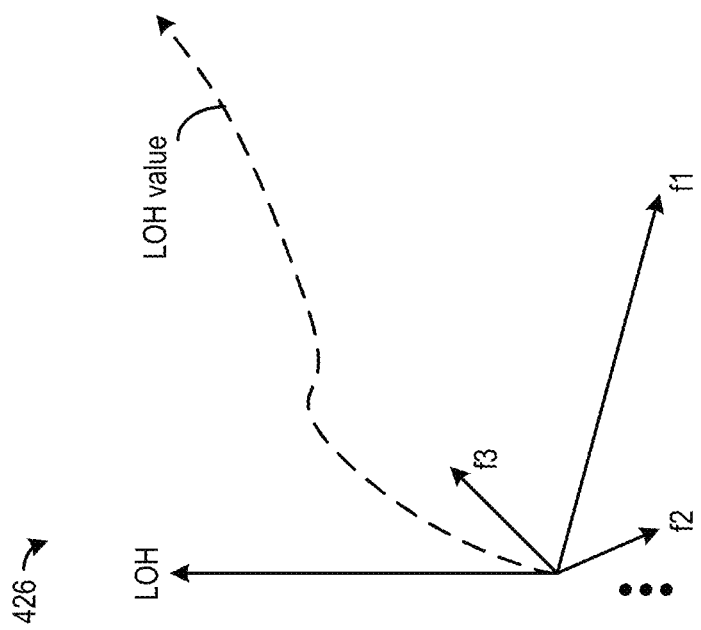

FIG. 4A and FIG. 4B illustrate examples of treatment metric model generation for segments of patients data. In FIG. 4A, a treatment metric model describing a relationship between a treatment metric and each patient feature can be determined, whereas FIG. 4B illustrates a treatment metric model that ranks the patient features based on their influence on a particular treatment metric.

Referring to FIG. 4A, as shown on graph 402, based on the results of the two-stage clustering operation of FIG. 3C and FIG. 3D, cluster 390a of patients data can be formed. Cluster 390a of patients data may include diagnosis data indicating whether the patients have experienced organ failure, as well as treatment administration data indicating whether the patients use a private insurance or a public insurance, which are included in patient features vector 301 and clustered by the two-stage clustering operation. In addition, cluster 390a of patients data may also include a set of treatment metric data, such as length of hospitalization (LOH) for patients of that cluster.

Graphs 404 and 406 illustrate example distributions of length of hospitalization (LOH) among patients having experienced organ failure (or no failure) and patients using public or private insurance can be extracted from patients data segment 310a. The distribution include a range of LOH as well as the distribution of the patients within the ranges. Specifically, in both graphs 404 and 406, the bars denote a range of LOHs for the patients having a particular feature within cluster 310a. For example, in graph 404, patients having private insurance have a range 408 of LOH, whereas patients having public insurance have a range 410 of LOH. Moreover, in graph 406, patients having organ failure have a range 412 of LOH, whereas patients not having organ failure have a range 414 of LOH.

Moreover, the ovals and their colors represent the number of patients within each subrange of the LOH ranges. For example, ovals 416 and 418 represent the numbers of patients within two subranges of LOH range 408, oval 420 represents the number of patients within a subrange of LOH range 410, ovals 422 and 424 represents the number of patients within two subranges of LOH range 412, whereas oval 427 represents the number of patients within a subrange of 414. The number of patients in oval 422 (black) can be higher than the other ovals (grey).

A correlation between LOH and a patient feature can be determined from graphs 404 and 406. For example, as shown in graph 404, the LOH ranges for patients having public insurance and the LOH ranges for patients having private insurance are about the same. Moreover, the density distributions of patients within the LOH range (represented by the color of the shading) are also about the same. This may indicate that the LOH have very little correlation with the type of insurance the patients have. Moreover, as shown in graph 406, the LOH ranges of patients having organ failure are higher than the LOH ranges of patients having no organ failure, with most of the patients having organ failure having a LOH close to the upper range (represented by oval 422). This may indicate that the LOH has a strong correlation with organ failure where patients having organ failure tend to have a longer LOH.

Supervised machine learning techniques, such as partial least square regression (PLSR), linear regression, etc., can be used to process the distributions of LOH exhibited in graphs 404 and 406 to determine, for example, a relationship between LOH and the insurance sources, and a relationship between LOH and patient's diagnosis result (e.g., whether the patient has organ failure). A function having LOH as a dependent variable and a data category (e.g., organ failure, insurance source, etc.) as an independent variable can be fit among that the data points of graphs 404 and 406 to describe the relationships. One example relationship can be represented by the following equation:

$$LOH = \alpha_1 \times f_1 + \alpha_2 \times f_2 + \alpha_3 \times f_3 \qquad \text{(Equation 1)}$$

Equation 1 can represent a LOH model based on a weighted sum of feature values $f_1$, $f_2$, and $f_3$. Feature value $f_1$ can represent whether the patient has private insurance or public insurance. Feature value $f_2$ can represent whether the patient has organ failure or has no organ failure. Feature value $f_3$ can represent a feature from treatment administration data 106 such as, for example, the hospital where the patient stayed for a treatment. These feature values can be non-binary and can be encoded using on one-hot encoding scheme to generate the feature values in patient features vectors 204. Weights $\alpha_1$, $\alpha_2$, and $\alpha_3$ can represent the weights assigned to, respectively, feature values $f_1$, $f_2$, and $f_3$.

FIG. 4B illustrates a LOH model 426 that provides different LOH values for different feature values $f_1$, $f_2$, and $f_3$. An LOH model can be computed based on the patients data for each of clusters 390 of patients data (e.g., cluster 390a, cluster 390b, cluster 390n, etc.).

Each of weights $\alpha_1$, $\alpha_2$, and $\alpha_3$ can represent a degree and a direction of influence of each respective feature values $f_1$, $f_2$, and $f_3$ on LOH. For example, based on graph 404, LOH has very little correlation with whether a patient has private insurance or public insurance, therefore the weight $\alpha_1$ assigned to feature value $f_1$ (which represents whether the patient has private insurance or public insurance) can have a very small value. Moreover, LOH has a strong and positive correlation with whether the patient has organ failure, therefore the weight $\alpha_2$ assigned to feature value $f_2$ (which represents whether the patient has organ failure) can be positive and have a large value.

LOH model 426 of FIG. 4B can be used to assist in generating a clinical decision. In one example, a new patient is accepted at a hospital, and a decision is to be made about selecting a treatment to be provided to the new patient (e.g., whether the new patient should be transferred to another hospital, etc.) out of a plurality of clinical options. The new patient may have patient features $f_1$ and $f_2$, but not $f_3$ (which represents the hospital to receive the treatment). The new patient data (and the new patient) can be classified into one of clusters 390 (e.g., cluster 390a). Various techniques of classification can be used. In one example, based on the patients data 204 in each of clusters 390, an average feature value for $f_1$ and for $f_2$ can be determined for each of clusters 390. The classification can be based on, for example, computing the Euclidean distances between the feature values $f_1$ and $f_2$ of the new patient and the average feature values $f_1$ and $f_2$ of each of clusters 390, and select one of clusters 390 for which the Euclidean distance is the minimum. The LOH model from the selected cluster can be used to determine whether the new patient should stay at that hospital or should be transferred to another hospital, with the objective of minimizing the LOH value. For example, different feature values $f_3$ representing different hospitals, in addition to the feature values $f_1$ and $f_2$, can be input to the LOH model to compute a set of LOH values. The hospital that give rise to the minimum LOH value according to the model can be selected to provide treatment to the new patient.

In some examples, as part of the treatment metric model, the data categories and/or features can be ranked based on their degree and direction of impacts on the treatment metric, which enable an application (e.g., a clinical decision making application, a medical resource management application, etc.) to identify data categories/features that exert the strongest impact on the treatment metric, and to generate a decision based on the identification. For example, treatment metric values for patients having a particular patient feature (e.g., being part of an age group) and treatment metric values for patients not having that patient feature (e.g., not part of the age group) can be determined. Based on the differences between these treatment metric values, the effect of absence or presence of that patient feature on the treatment metric category can be determined. Other techniques, such as Variables Importance on Partial Least Squares (PLS) projections (VIP), can also be employed.

Figure 4C:
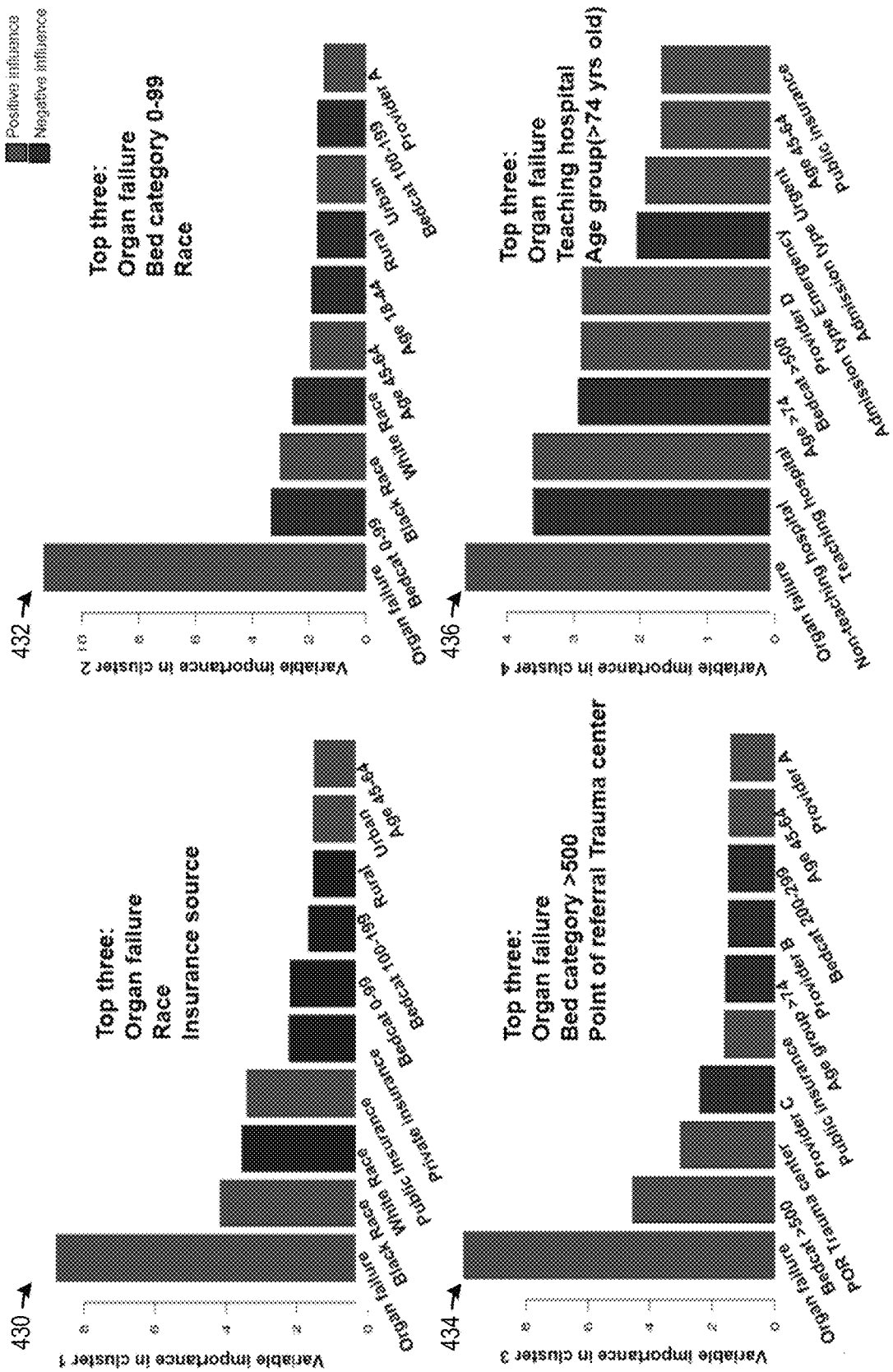

FIG. 4C illustrates graphs 430, 432, 434, and 436 of the ranking of impact of different features on LOH for different clusters 390 of patient data based on VIS. Cluster 1 can correspond to cluster 390a of patients data, cluster 2 can correspond to cluster 390b of patients data, cluster 3 can correspond to cluster 390c of patients data, whereas cluster 4 can correspond to cluster 390d of patients data. As shown in graph 430, for cluster 1, the top three data categories that exert the strongest impact on LOH are organ failure, race, and source of insurance. For cluster 2, the top three data categories that exert the strongest impact on LOH are organ failure, a number of beds between 0-99 (of the hospital in which the patient received treatment), and race. For cluster 3, the top three data categories that exert the strongest impact on LOH are organ failure, a number of beds over 500 (of a hospital in which the patient received treatment), and point of referral being a trauma center. For cluster 4, the top three data categories that exert the strongest impact on LOH are organ failure, the patient received treatment at a teaching hospital, and the patient in an age group over 75.

As shown in FIG. 4C, some features, such as organ failure, can exert a large degree of impact on LOH in different clusters of patients, whereas some other features, such as being treated at a non-teaching hospital, exerts a large degree of impact on LOH for a particular cluster (cluster 4) but not in other clusters. The relationship between a certain feature and LOH may depend on other features of the patients, such as the patients' demographic characteristics, various aspects of treatment administration, etc. Moreover, hidden factors, such as bias, may be identified in a case where some factors exert significant impacts on the LOH, and those factors are not strongly related to the severity of the disease or the quality of treatment. For example, race and insurance source exert strong impact on LOH in cluster 1. It may be determined that these factors are not strongly related to the severity of the disease or the quality of treatment, and their impacts on LOH can be due to those hidden factors.

The ranking of features in a treatment metric model can be used to assist in generating a clinical decision. For example, as shown in FIG. 4C, the model may indicate that staying in a non-teaching hospital has a large and negative influence on the length of hospitalization in cluster 3. In such a case, a decision can be made to transfer the new patient to a non-training hospital to reduce the length of hospitalization for the patient, which can also reduce the economic burden on the patient. As another example, if the new patient has features matching the highest ranked features in the model, the clinical decision can be made based on the influences of those features. For example, the model may indicate that being part of a particular age group has a large and positive influence on the length of hospital stay, which may suggest that patients in that age group tends to stay in the hospital longer to recover. If the new patient is also in that age group, a decision can be made to extend the length of hospitalization for the new patient.

The ranking of features in a treatment metric model can also be used to improve medical resource management by, for example, identifying administrative factors that impact the treatment metrics but are unrelated to the severity of the illness. For example, for a cluster of patients, the model may indicate that staying at a specific hospital has a large and positive influence on the length of hospitalization at that hospital, while the severity of the illness has a relatively small impact on the length of hospitalization at that hospital. Based on this indication, inquiries specific to that hospital can be made to determine the causes for the longer length of hospitalization, and to determine which action (e.g., more training, more equipment, etc.) can be undertaken to shorten the length of hospitalization for the patients there.

IV. Applications of Treatment Metric Model

Figure 5A:
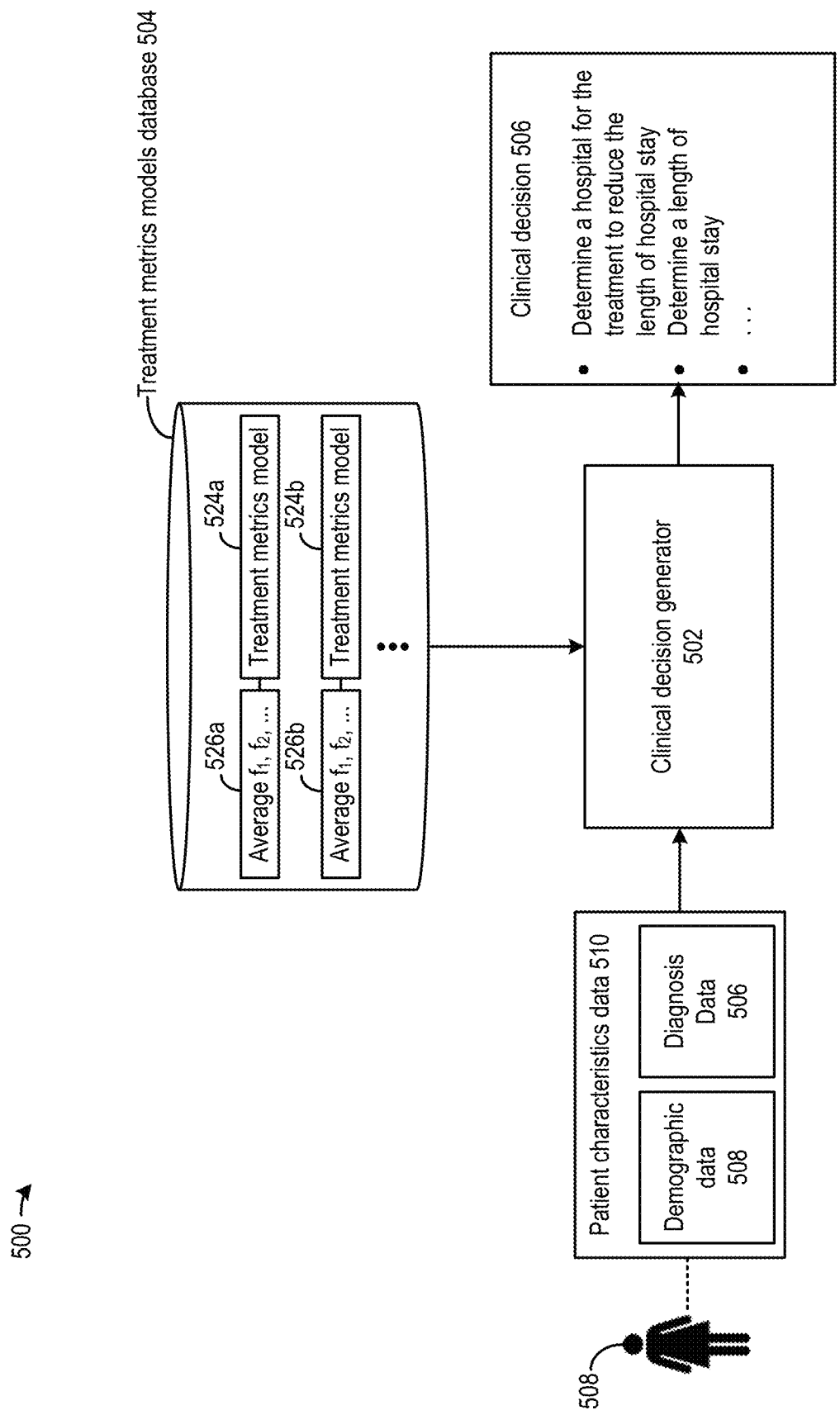
FIG. 5A and FIG. 5B illustrate examples of applications of treatment metric model, according to certain aspects of this disclosure.
Figure 5B:
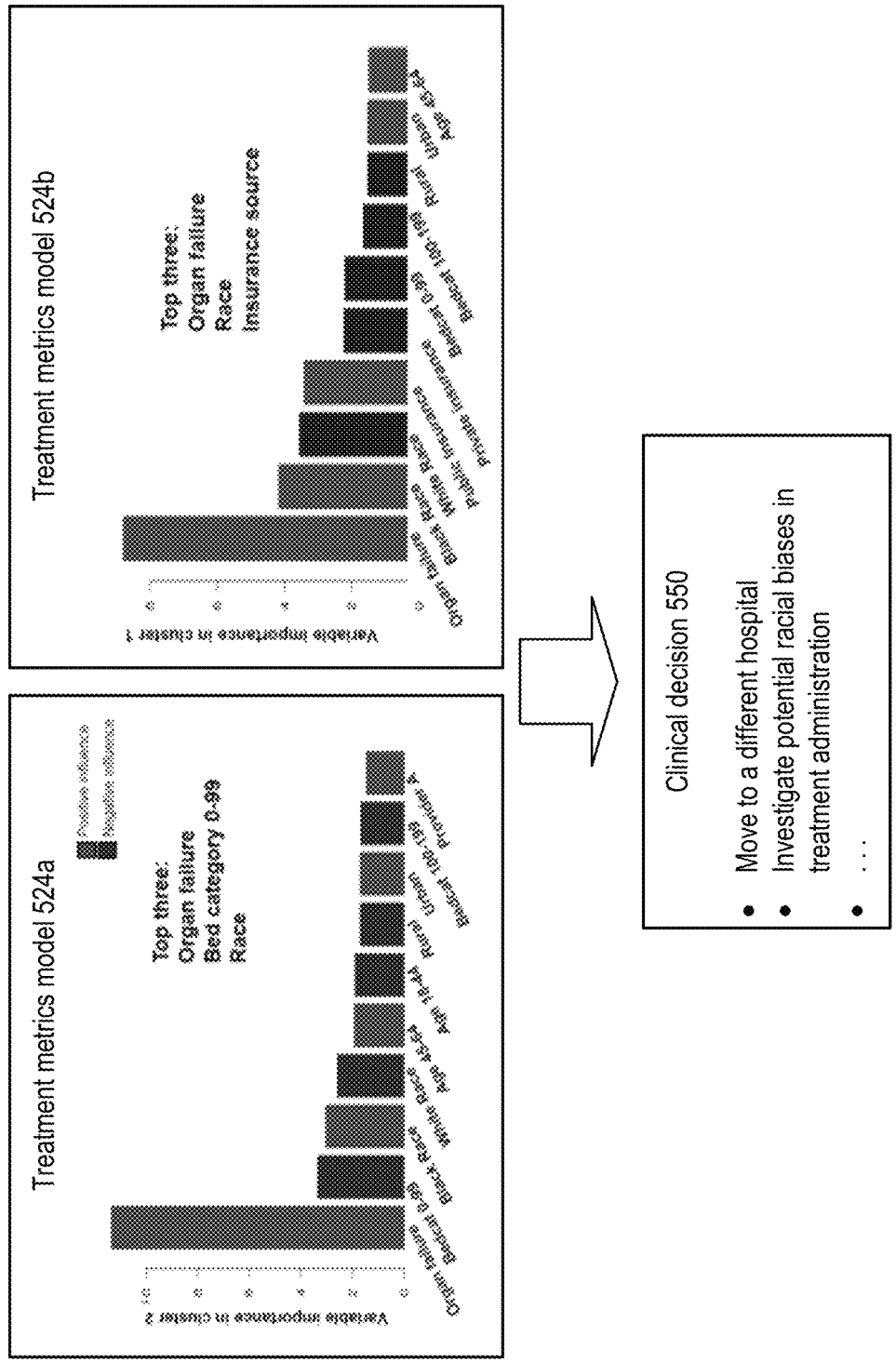

FIG. 5A and FIG. 5B illustrate examples of applications of treatment metric models generated using the disclosed techniques. FIG. 5A illustrates an example of using a treatment metric model to support clinical decision making, based on techniques described above in FIG. 4A-FIG. 4C. As shown in FIG. 5A, a system 500, which includes a clinical decision generator 502 and a treatment metric models database 504, can generate one or more clinical decisions 506 (or recommendations) for a new patient 508 based on patient characteristics data 510 of new patient.

As shown in FIG. 5A, patient characteristics data 510 may include demographic data 518 and diagnosis data 520 having the same categories of data/features (e.g., age group 320, gender 326, organ failure 330, etc.) as, respectively, demographic data 205 and diagnosis data 206 of FIG. 2. In addition, treatment metric models database 504 stores a plurality of treatment metric models 524 including, for example, treatment metric model 524a, treatment metric model 524b, etc. Each treatment metric model can be generate based on a cluster 390 of patients data 204 (e.g., cluster 390a, cluster 390b, cluster 390n, etc.) from the two-stage clustering operation of FIG. 3C. Each treatment metric model is associated with a set of average feature values (e.g., $f_1$ $f_2$, etc.) of the respective cluster. For example, treatment metric model 524a is associated with average feature values 526a, whereas treatment metric model 524b is associated with average feature values 526b. Treatment metric models 524 can include models that describe relationships between a treatment metric (e.g., LOH) and the feature values, such as LOH model 426 of FIG. 4B. Treatment metric model 524 can also include models that rank the impact of different features on a treatment metric (e.g., LOH), such as those shown in FIG. 4C.

Clinical decision generator 502 can identify a treatment metric model from treatment metric models database 504 based on patient characteristics data 510, and use the identified treatment metric model to generate clinical decisions 506 (or recommendations) for new patient 508. The identification can be based on determining, from database 504, a set of average feature values that are of the minimum Euclidean distance from patient characteristics data 510. The treatment metric model associated with the identified set of average feature values can then be identified.

Clinical decision generator 502 can use the identified treatment metric model to generate (or to assist in generating) a clinical decision. For example, a new patient is accepted at a hospital, and a decision is to be made about selecting a treatment to be provided to the new patient (e.g., whether the new patient should be transferred to another hospital, etc.) out of a plurality of clinical options. Clinical decision generator 502 can input feature values of patient characteristics data 510 of the new patient to the identified model. Clinical decision generator 502 can also input a range of feature values of treatment administration data representing the clinical options, such as different hospitals, to the identified model, to generate a set of treatment metric values (e.g., a set of LOH values). The hospital that give rise to the minimum LOH value according to the model can be selected to provide treatment to the new patient.

FIG. 5B illustrates other applications of treatment metric models. In FIG. 5B, the treatment metric models may include those shown in FIG. 4C and include a ranking of features based on their impact on a treatment metric such as LOH. In FIG. 5B, clinical decision generator 502 may identify treatment metric model 524a based on patient characteristics data 510 and generate a clinical decision 550. For example, from treatment metric model 524a, clinical decision generator 502 may determine that receiving treatment in a hospital having fewer than 100 beds (represented by "Bedcat 0-99") is one of the top-ranked feature and has a negative influence on LOH. To reduce LOH, a clinical decision 550 can be made to transfer the new patient to a hospital having fewer than 100 beds. In another example, both treatment metric models 524a and 524b indicate that race is one of the top three factors having the strongest impact on LOH. If there is a lack of clear connection between race and LOH, a clinical decision 550 can be made to devote medical resources to investigate whether there exists some form of racial bias in the treatment administration by the hospitals represented in the patients data.

V. Method

Figure 6:
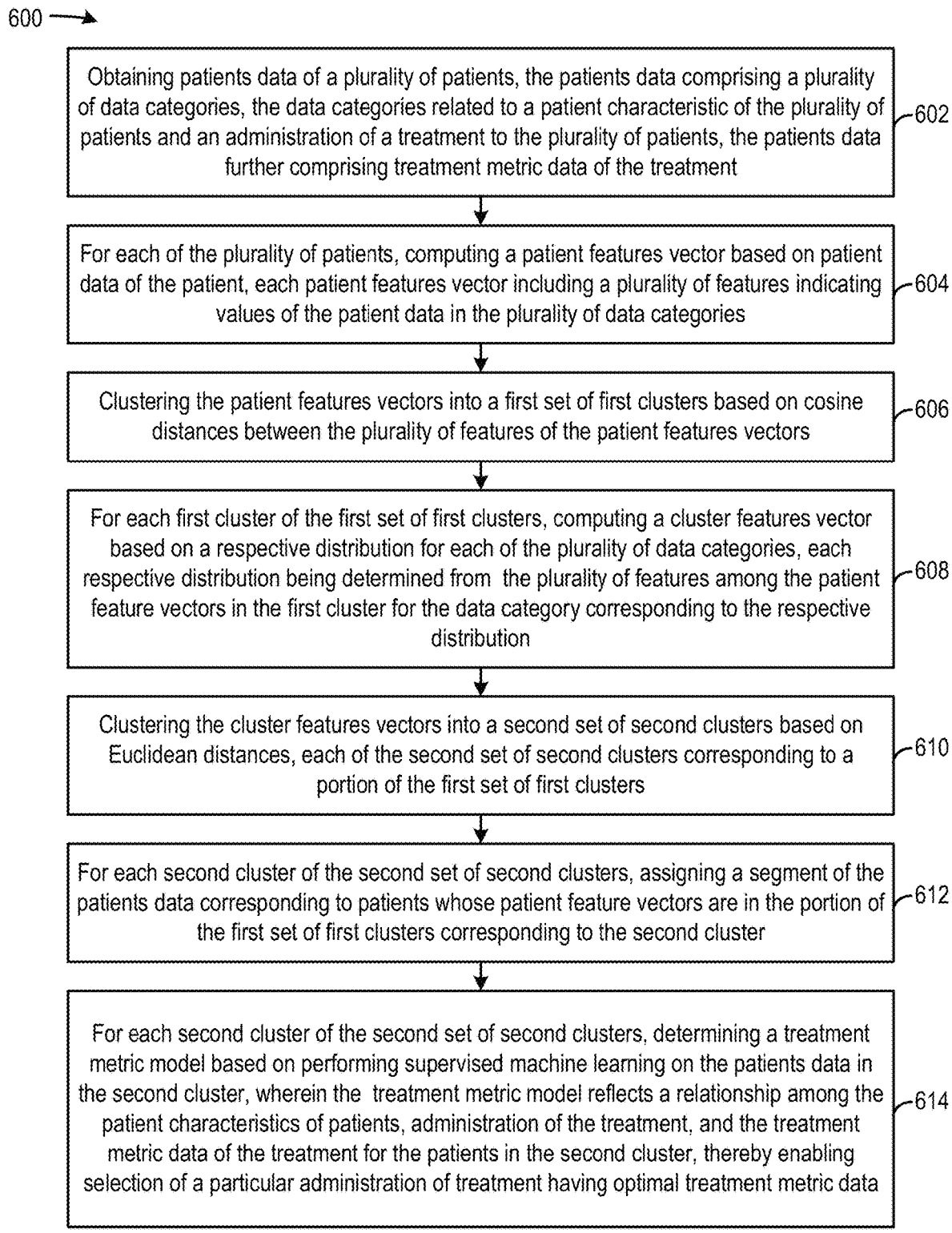
FIG. 6 illustrates a method of performing determining a treatment metric model, according to certain aspects of this disclosure.

FIG. 6 illustrates a method 600 of determining a treatment metric model. Method 600 can be performed by, for example, a computer.

At operation 602, the computer may obtain patients data of a plurality of patients, the patients data comprising a plurality of data categories related to characteristics of the patients and administration of treatments to the patients, the profile data further comprising treatment metric data of the treatments. The patients may have contracted a common illness (e.g., sepsis), have received medical treatments for the illness, and have since recovered. The patients data of each patient may include characteristics data each patient, administration data related to the treatment each patient has received, as well as treatment metrics data related to the medical treatments. The characteristics data and the administration data may be associated with a plurality of data categories. The characteristics data may include different categories of data including, for example, demographic data (which may include categories such as age, gender, race, etc.), locale (which may include categories such as city of residence, urban or rural area, etc.), etc. the diagnosis results of the patient before and/or during the medical treatment, etc. The diagnosis results may be specific to the illness and may include categories of data indicating, for example, whether the patient suffered from an organ failure, whether the patient has contracted an inflection, etc. Moreover, the administration data may include categories of data identifying, for example, the hospital where the patient stayed for the medical treatment, whether the hospital is a teaching hospital or non-teaching hospital, a number of inpatient beds of the hospital, insurance provider information, etc. The treatment metrics data may include, for example, a length of hospitalization (LOH) of the patient for the medical treatment, cost, and other metrics to evaluate the quality of the medical treatment (e.g., recurrence of the illness, etc.).

At operation 604, the computer may compute a patient features vector, such as patient features vectors 301, for each of the plurality of patients based on the patient data, each patient features vector including a plurality of features corresponding to the plurality of data categories of the patients data. As shown in FIG. 3A, each feature can be a one-hot encoded representation of a value of a corresponding data category. The value can be one of a discrete set of alternative values for the data category, and the one-hot encoded representation can indicate which of the alternative value that data category has taken.

At operation 606, the computer system may cluster the patient features vectors into a first set of first clusters based on cosine distances between the plurality of features of the patient features vector. For example, the clustering can be performed so that the cosine distance between any two patient features vectors within a cluster is below a first threshold (e.g., corresponding to 50% difference or less).

At operation 608, the computer may compute a cluster features vector, such as cluster features vectors 305, for each first cluster of the first set of first clusters, each cluster features vector being computed based on a distribution for each of the plurality of data categories. Each respective distribution is determined from the plurality of features among the patient feature vectors in the first cluster for the data category corresponding to the respective distribution. The distribution can be based on, for example, a percentage of occurrence of each alternative values for each data category/feature in the cluster. Each cluster features vector may represent a sample of a cluster of the first set of first clusters. Computing a cluster features vector for each cluster of the first set of first clusters, each cluster features vector being computed based on a distribution of the plurality of features in the each cluster At operation 610, the computer may cluster the cluster features vectors into a second set of second clusters based on Euclidean distance clustering. Each cluster feature vectors may include numerical representations of the features, and Euclidean distances can be computed based on the numerical representations. For example, the clustering can be performed so that the Euclidean distance between any two cluster features vectors within a cluster is below a second threshold.

At operation 612, the computer may, for each second cluster of the second set of second clusters, assign a segment of the patients data corresponding to patients whose patient feature vectors are in the portion of the first set of first clusters corresponding to the second cluster. The patients data can be mapped to the cluster features vectors via patient features vectors and can be divided according to the second set of second clusters, as shown in FIG. 3D.

At operation 614, the computer may, for each second cluster of the second set of second clusters, determine a treatment metric model based on performing supervised machine learning on the patients data in the second cluster. The treatment metric model reflects a relationship among the patient characteristics of patients, administration of the treatment, and the treatment metric data of the treatment for the patients in the second cluster, thereby enabling selection of a particular administration of treatment having optimal treatment metric data. The supervised machine learning may include, for example, partial least square regression (PLSR), linear regression, etc. A function having the treatment metric as a dependent variable and a data category (e.g., organ failure, insurance source, etc.) as an independent variable can be fitted among that the data points of the patients data in each cluster to describe the relationships. The treatment metric models can include, for example, a relationship between a treatment metric and patient characteristics, treatment administration features, etc. The treatment metric models can also include a ranking of data categories based on the degrees of impact of the data categories on the treatment metric.

In some examples, method 600 further comprises selecting an administration of treatment by: classifying a new patient into one of the second set of second clusters based on the patient characteristics data of the new patient; obtaining a first treatment metric model determined for the one of the second set of second clusters; inputting the patient characteristics data and data representing a range of administrations of the treatment to the first treatment metric model to compute a range of treatment metrics; and selecting, as part of the clinical decision, an administration of the treatment from the range of administrations of the treatment based on the range of treatment metrics. For example, a clinical decision can be made to reduce length of hospitalization based on identifying, from a treatment metric model of a cluster that is most similar to a new patient, factors that exert the strongest impacts on the treatment metric for the new patient. As another example, a resource management decision can be made to identify factors that impact treatment metrics but not related severity of the illness or quality of care.

VI. Additional Embodiments

In one example, a method comprises: obtaining patients data of a plurality of patients, the patients data comprising a plurality of data categories related to characteristics of the patients and administration of a treatment to the patients, the patients data further comprising treatment outcome data of the treatment; computing a patient features vector for each of the plurality of patients based on the patients data, each patient features vector including a plurality of features corresponding to the plurality of data categories of the patients data; clustering the patient features vectors into a first set of clusters based on cosine distances; computing a cluster features vector for each cluster of the first set of clusters, each cluster features vector being computed based on a distribution of the plurality of features in the each cluster; clustering the cluster features vectors into a second set of clusters based on Euclidean distances; dividing the patients data into the second set of clusters; and determining a treatment outcome model for each cluster of the second set of clusters based on performing supervised machine learning on the each cluster of patients data.

In one example, a method comprises: obtaining patients data of a plurality of patients, the patients data comprising a plurality of data categories, the data categories related to a patient characteristic of the plurality of patients and an administration of a treatment to the plurality of patients, the patients data further comprising treatment metric data of the treatment; for each of the plurality of patients, computing a patient features vector based on patient data of the patient, each patient features vector including a plurality of features indicating values of the patient data in the plurality of data categories; clustering the patient features vectors into a first set of first clusters based on cosine distances between the plurality of features of the patient features vectors; for each first cluster of the first set of first clusters, computing a cluster features vector based on a respective distribution for each of the plurality of data categories, each respective distribution being determined from the plurality of features among the patient feature vectors in the first cluster for the data category corresponding to the respective distribution; clustering the cluster features vectors into a second set of second clusters based on Euclidean distances, each of the second set of second clusters corresponding to a portion of the first set of first clusters; for each second cluster of the second set of second clusters, assigning a segment of the patients data corresponding to patients whose patient feature vectors are in the portion of the first set of first clusters corresponding to the second cluster; for each second cluster of the second set of second clusters, determining a treatment metric model based on performing supervised machine learning on the patients data in the second cluster, wherein the treatment metric model reflects a relationship among the patient characteristics of patients, administration of the treatment, and the treatment metric data of the treatment for the patients in the second cluster. Each of the treatment metric models enables a treatment metric to be computed for a new patient based on inputting patient characteristic data of the new patient, and a clinical decision to be generated for the new patient based on the computed treatment metric.

In some aspects, the method further comprises selecting the particular administration of treatment by: classifying the new patient into one of the second set of second clusters based on the patient characteristics data of the new patient; obtaining a first treatment metric model determined for the one of the second set of second clusters; inputting the patient characteristics data and data representing a range of administrations of the treatment to the first treatment metric model to compute a range of treatment metrics; and selecting, as part of the clinical decision, an administration of the treatment from the range of administrations of the treatment based on the range of treatment metrics.

In some aspects, the treatment metric comprises a length of hospitalization (LOH).

In some aspects, the plurality of data categories comprise demographic data of a patient and diagnosis data of the patient prior to the administration of the treatment to the patient.

In some aspects, the demographic data comprise at least one of: age group, marital status, race, gender, or locale.

In some aspects, the diagnosis data comprise at least one of: whether the patient experiences organ failure, or whether the patient experiences infection.

In some aspects, the data categories related to the administration of the treatment to a patient comprise: a type of admission of the patient to a hospital, a source of insurance, an operator of the hospital, a type of the hospital, a number of beds of the hospital, or a point of referral.

In some aspects, a feature included in a patient feature vector indicates one of a discrete set of alternative values of a corresponding data category.

In some aspects, for each cluster of the first set of first clusters and for each of the plurality of data categories, the distribution comprises a percentage of occurrence in the patient feature vectors for each alternative value of the corresponding data category.

In some aspects, the feature comprises a discrete set of bits and is one-hot encoded to indicate which of the discrete set of alternative values is the value. Each of the patient features vectors comprise only binary values.

In some aspects, a cosine distance between any two of the patient features vectors in a cluster of the first set of first clusters is below a first threshold.

In some aspects, a Euclidean distance between any two of the cluster features vectors in a cluster of the second set of second clusters is below a second threshold.

In some aspects, the supervised machine learning comprises at least one of: partial least square regression (PLSR), or linear regression.

In some aspects, the treatment metric model comprises a ranking of the plurality of data categories based on degrees of impact of the plurality of data categories.

In some aspects, the plurality of patients comprise at least a thousand patients.

VII. Computer System

Figure 7:
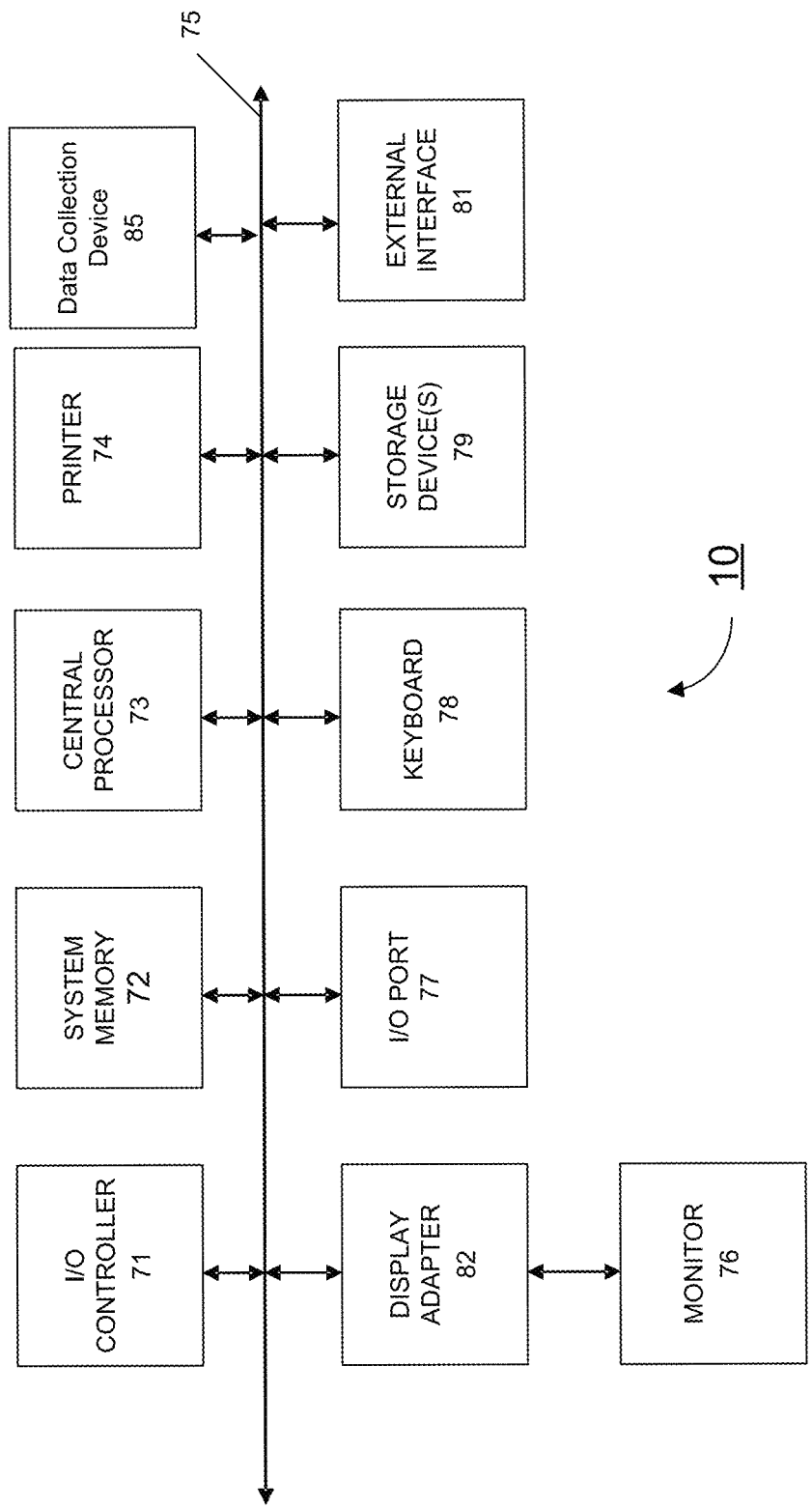
FIG. 7 illustrates an example computer system that may be utilized to implement techniques disclosed herein.

Any of the computer systems mentioned herein may utilize any suitable number of subsystems. Examples of such subsystems are shown in FIG. 7 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices. In some embodiments, a cloud infrastructure (e.g., Amazon Web Services), a graphical processing unit (GPU), etc., can be used to implement the disclosed techniques.

The subsystems shown in FIG. 7 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A method, comprising:
    obtaining patients data of a plurality of patients, the patients data comprising a plurality of data categories, the data categories related to a patient characteristic of the plurality of patients and an administration of a treatment to the plurality of patients, wherein the data categories related to the administration of the treatment to a patient comprise one or more of a group consisting of: a type of admission of the patient to a hospital, a source of insurance, an operator of the hospital, a type of the hospital, a number of beds of the hospital, and a point of referral, the patients data further comprising treatment metric data of the treatment, wherein the treatment metric data reflects results of the treatment for the plurality of patients;
    for each of the plurality of patients, computing a patient features vector based on patient data of the patient, each patient features vector including a plurality of features indicating values of the patient data in the plurality of data categories;
    clustering the patient features vectors into a first set of first clusters based on cosine distances between the plurality of features of the patient features vectors;
    for each first cluster of the first set of first clusters, computing a cluster features vector based on a respective distribution for each of the plurality of data categories, each respective distribution being determined from the plurality of features among the patient features vectors in the first cluster for the data category corresponding to the respective distribution;
    clustering the cluster features vectors into a second set of second clusters based on Euclidean distances, each of the second set of second clusters corresponding to a portion of the first set of first clusters;
    for each second cluster of the second set of second clusters, assigning a segment of the patients data corresponding to patients whose patient feature vectors are in the portion of the first set of first clusters corresponding to the second cluster; and
    for each second cluster of the second set of second clusters, determining a treatment metric model based on performing supervised machine learning on the patients data in the second cluster using a function having the treatment metric as a dependent variable and a data category as an independent variable, wherein the treatment metric model reflects a relationship among the patient characteristics of patients, administration of the treatment, and the treatment metric data of the treatment for the patients in the second cluster, thereby enabling selection of a particular administration of treatment having optimal treatment metric data.

2. The method of claim 1, further comprising selecting the particular administration of treatment by:
    classifying a new patient into one of the second set of second clusters based on patient characteristics data of the new patient;
    obtaining a first treatment metric model determined for the one of the second set of second clusters;
    inputting the patient characteristics data and data representing a range of administrations of the treatment to the first treatment metric model to compute a range of treatment metric data; and
    selecting, as part of a clinical decision, an administration of the treatment from the range of administrations of the treatment based on the range of treatment metric data.

3. The method of claim 1, wherein the treatment metric data comprises a length of hospitalization (LOH).

4. The method of claim 1, wherein the plurality of data categories comprise demographic data of a patient and diagnosis data of the patient prior to the administration of the treatment to the patient.

5. The method of claim 4, wherein the demographic data comprise at least one of: age group, marital status, race, gender, or locale.

6. The method of claim 4, wherein the diagnosis data comprise at least one of: whether the patient experiences organ failure, or whether the patient experiences infection.

7. The method of claim 1, wherein a feature included in a patient feature vector indicates one of a discrete set of alternative values of a corresponding data category.

8. The method of claim 7, wherein, for each cluster of the first set of first clusters and for each of the plurality of data categories, the distribution comprises a percentage of occurrence in the patient feature vectors for each alternative value of the corresponding data category.

9. The method of claim 7, wherein the feature comprises a discrete set of bits and is one-hot encoded to indicate which of the discrete set of alternative values is the value; and
    wherein each of the patient features vectors comprise only binary values.

10. The method of claim 1, wherein a cosine distance between any two of the patient features vectors in a cluster of the first set of first clusters is below a first threshold.

11. The method of claim 1, wherein a Euclidean distance between any two of the cluster features vectors in a cluster of the second set of second clusters is below a second threshold.

12. The method of claim 1, wherein the supervised machine learning comprises at least one of: partial least square regression (PLSR), or linear regression.

13. The method of claim 1, wherein the treatment metric model comprises a ranking of the plurality of data categories based on degrees of impact of the plurality of data categories.

14. The method of claim 1, wherein the plurality of patients comprise at least a thousand patients.

15. An apparatus comprising:
    a treatment metric model database that stores a plurality of treatment metric models, wherein each of the plurality of treatment metric models is associated with a plurality of patient characteristics features in the treatment metric model database, and wherein each of the plurality of treatment metric models is generated for a first cluster of cluster features vectors, each cluster feature vector representing a distribution for each of a plurality of data categories of patients data represented by patient feature vectors clustered in a second cluster, the data categories being related to a patient characteristic of the plurality of patients and an administration of a treatment to the plurality of patients, wherein the data categories related to the administration of the treatment to a patient comprise one or more of a group consisting of: a type of admission of the patient to a hospital, a source of insurance, an operator of the hospital, a type of the hospital, a number of beds of the hospital, and a point of referral;

a memory that stores a set of instructions; and a hardware processor configured to:
  receive patient characteristics features data of a patient;
  identify, based on comparing the patient characteristics features data of the patient and the plurality of patient characteristics features associated with each of the plurality of treatment metric models, a first treatment metric model based on performing supervised machine learning on the patients data in the second cluster using a function having the treatment metric as a dependent variable and a data category as an independent variable;
  input the patient characteristic features data and data representing a range of administrations of the treatment to the first treatment metric model to compute a range of treatment metric data, wherein the treatment metric data reflects results of the treatment for the patient; and
    select, as part of a clinical decision for the patient, an administration of the treatment from the range of administrations of the treatment having optimal treatment metric data.

16. The apparatus of claim 15, wherein the treatment metric data comprise a length of hospitalization (LOH).

17. The apparatus of claim 15, wherein the plurality of data categories comprise demographic data of a patient and diagnosis data of the patient prior to the administration of the treatment to the patient.

18. A non-transitory computer readable medium storing instructions that, when executed by a hardware processor, causes the hardware processor to:
  obtain patients data of a plurality of patients, the patients data comprising a plurality of data categories, the data categories related to a patient characteristic of the plurality of patients and an administration of a treatment to the plurality of patients, the patients data further comprising treatment metric data of the treatment, the patients data comprising a plurality of data categories, the data categories related to a patient characteristic of the plurality of patients and an administration of a treatment to the plurality of patients, wherein the data categories related to the administration of the treatment to a patient comprise one or more of a group consisting of: a type of admission of the patient to a hospital, a source of insurance, an operator of the hospital, a type of the hospital, a number of beds of the hospital, and a point of referral, wherein the treatment metric data reflects results of the treatment for the plurality of patients;
  for each of the plurality of patients, compute a patient features vector based on patient data of the patient, each patient features vector including a plurality of features indicating values of the patient data in the plurality of data categories;
  cluster the patient features vectors into a first set of first clusters based on cosine distances between the plurality of features of the patient features vectors;
  for each first cluster of the first set of first clusters, compute a cluster features vector based on a respective distribution for each of the plurality of data categories, each respective distribution being determined from the plurality of features among the patient features vectors in the first cluster for the data category corresponding to the respective distribution;
  cluster the cluster features vectors into a second set of second clusters based on Euclidean distances, each of the second set of second clusters corresponding to a portion of the first set of first clusters;
  for each second cluster of the second set of second clusters, assign a segment of the patients data corresponding to patients whose patient feature vectors are in the portion of the first set of first clusters corresponding to the second cluster; and
  for each second cluster of the second set of second clusters, determine a treatment metric model based on performing supervised machine learning on the patients data in the second cluster using a function having the treatment metric as a dependent variable and a data category as an independent variable, wherein the treatment metric model reflects a relationship among the patient characteristics of patients, administration of the treatment, and the treatment metric data of the treatment for the patients in the second cluster, thereby enabling selection of a particular administration of treatment having optimal treatment metric data.

19. The non-transitory computer readable medium of claim 18, further storing instructions that, when executed by a hardware processor, causes the hardware processor to:
  classify a new patient into one of the second set of second clusters based on patient characteristics data of the new patient;
  obtain a first treatment metric model determined for the one of the second set of second clusters;
  input the patient characteristics data and data representing a range of administrations of the treatment to the first treatment metric model to compute a range of treatment metrics; and
  select, as part of a clinical decision, an administration of the treatment from the range of administrations of the treatment based on the range of treatment metrics.

* * * * *